US011179123B2

(12) United States Patent
Kitano

(10) Patent No.: US 11,179,123 B2
(45) Date of Patent: Nov. 23, 2021

(54) RADIOGRAPHY APPARATUS, RADIOGRAPHY APPARATUS OPERATION METHOD, AND RADIOGRAPHY APPARATUS OPERATION PROGRAM

(71) Applicant: FUJIFILM CORPORATION, Tokyo (JP)

(72) Inventor: Kouichi Kitano, Kanagawa (JP)

(73) Assignee: FUJIFILM CORPORATION, Tokyo (JP)

(*) Notice: Subject to any disclaimer, the term of this patent is extended or adjusted under 35 U.S.C. 154(b) by 41 days.

(21) Appl. No.: 16/830,270

(22) Filed: Mar. 26, 2020

(65) Prior Publication Data
US 2020/0305817 A1 Oct. 1, 2020

(30) Foreign Application Priority Data
Mar. 29, 2019 (JP) .............................. JP2019-067608

(51) Int. Cl.
*A61B 6/00* (2006.01)
*G06T 7/00* (2017.01)
*G06T 5/50* (2006.01)

(52) U.S. Cl.
CPC .............. *A61B 6/482* (2013.01); *A61B 6/44* (2013.01); *A61B 6/486* (2013.01); *A61B 6/505* (2013.01); *A61B 6/5205* (2013.01); *A61B 6/5252* (2013.01); *A61B 6/5264* (2013.01); *A61B 6/541* (2013.01); *A61B 6/548* (2013.01); *G06T 5/50* (2013.01); *G06T 7/0012* (2013.01)

(58) Field of Classification Search
CPC .......... A61B 6/405; A61B 6/44; A61B 6/482; A61B 6/486; A61B 6/50; A61B 6/505; A61B 6/5205; A61B 6/5252; A61B 6/5264; A61B 6/541; A61B 6/548; G06T 5/50; G06T 7/0012
See application file for complete search history.

(56) References Cited

U.S. PATENT DOCUMENTS

| 6,252,932 B1* | 6/2001 | Arakawa .............. A61B 6/4035 378/98.11 |
| 7,085,351 B2* | 8/2006 | Lu .......................... A61B 6/482 378/122 |

(Continued)

FOREIGN PATENT DOCUMENTS

JP 2011-067333 A 4/2011

*Primary Examiner* — Dani Fox
*Assistant Examiner* — Soorena Kefayati
(74) *Attorney, Agent, or Firm* — Solaris Intellectual Property Group, PLLC

(57) ABSTRACT

In a case in which an imaging mode continuously acquiring a plurality of energy subtraction images is performed, a radiation source control unit of a control device performs radiation source control for performing a one-shot imaging operation, in which only one of first radiation and second radiation is emitted, at least once for one two-shot imaging operation in which the first radiation and the second radiation are continuously emitted. In a case in which the imaging mode is performed, a detector control unit performs detector control to direct a radiation detector to output a first radiographic image based on the first radiation and a second radiographic image based on the second radiation.

11 Claims, 18 Drawing Sheets

(56) References Cited

U.S. PATENT DOCUMENTS

| | | | | |
|---|---|---|---|---|
| 8,571,178 B2* | 10/2013 | Sendai | ............... | A61B 6/482 |
| | | | | 378/98.9 |
| 2005/0220270 A1* | 10/2005 | Kameshima | ............ | A61B 6/00 |
| | | | | 378/116 |
| 2008/0232667 A1* | 9/2008 | Kitamura | ............... | G06K 9/54 |
| | | | | 382/132 |
| 2009/0016492 A1* | 1/2009 | Tsuchiya | ............ | H04N 5/3205 |
| | | | | 378/98.9 |
| 2009/0060312 A1* | 3/2009 | Kitamura | ............ | G06T 7/0012 |
| | | | | 382/132 |
| 2009/0323896 A1* | 12/2009 | Kitamura | ............... | A61B 6/00 |
| | | | | 378/98.11 |
| 2010/0067772 A1* | 3/2010 | Kitamura | ............ | G01T 1/1647 |
| | | | | 382/132 |
| 2011/0075810 A1* | 3/2011 | Sendai | ................ | G21K 1/10 |
| | | | | 378/95 |
| 2012/0008735 A1* | 1/2012 | Maurer | ............... | A61B 6/025 |
| | | | | 378/5 |
| 2013/0136331 A1* | 5/2013 | Hoernig | ............... | A61B 6/025 |
| | | | | 382/132 |
| 2014/0185759 A1* | 7/2014 | Kang | ................ | A61B 6/482 |
| | | | | 378/62 |
| 2014/0243579 A1* | 8/2014 | Roeske | ............... | A61B 6/485 |
| | | | | 600/1 |
| 2016/0267651 A1* | 9/2016 | Maack | ............... | G06K 9/6215 |
| 2016/0350910 A1* | 12/2016 | Jeong | ................ | G06K 9/52 |
| 2017/0116730 A1* | 4/2017 | Yamanaka | ............ | G06T 5/008 |
| 2017/0340305 A1* | 11/2017 | Bertens | ............... | G06T 7/337 |
| 2018/0031714 A1* | 2/2018 | Tajima | ............... | A61B 6/4266 |
| 2018/0068422 A1* | 3/2018 | Kawamura | ............ | G06T 5/50 |
| 2018/0068442 A1* | 3/2018 | Kawamura | ............ | G06T 5/50 |
| 2018/0068468 A1* | 3/2018 | Kawamura | ............ | G06T 11/00 |
| 2018/0128755 A1* | 5/2018 | Iwashita | ............ | A61B 6/4233 |

\* cited by examiner

FIG. 19

| 1 | 2 | 3 | 4 | 5 | 6 | 7 | 8 | |
|---|---|---|---|---|---|---|---|---|
| TWO-SHOT IMAGING | ONE-SHOT IMAGING | ONE-SHOT IMAGING | ONE-SHOT IMAGING | TWO-SHOT IMAGING | ONE-SHOT IMAGING | ONE-SHOT IMAGING | ONE-SHOT IMAGING | ... |

RADIOGRAPHY APPARATUS, RADIOGRAPHY APPARATUS OPERATION METHOD, AND RADIOGRAPHY APPARATUS OPERATION PROGRAM

CROSS-REFERENCE TO RELATED APPLICATIONS

The present application claims priority under 35 U.S.C. § 119 to Japanese Patent Application No. 2019-067608 filed on Mar. 29, 2019. The above application is hereby expressly incorporated by reference, in its entirety, into the present application.

BACKGROUND

1. Technical Field

A technology of the present disclosure relates to a radiography apparatus, a radiography apparatus operation method, and a radiography apparatus operation program.

2. Description of the Related Art

In the field of medical radiography, radiography apparatuses have been known which perform energy subtraction (hereinafter, abbreviated to ES) imaging (for example, see JP2011-067333A). As described in JP2011-067333A, the ES imaging is an imaging method which directs a radiation source to continuously emit first radiation and second radiation having different energy distributions and directs a radiation detector to output a first radiographic image based on the first radiation and a second radiographic image based on the second radiation. Hereinafter, the ES imaging method that continuously emits the first radiation and the second radiation is referred to as two-shot imaging.

It is possible to generate an ES image in which a structure in a subject has been highlighted on the basis of the first radiographic image and the second radiographic image. Specifically, the pixel value of each of the first radiographic image and the second radiographic image is multiplied by an appropriate weighting coefficient and then the difference between the pixel values is calculated to generate an ES image. Examples of the structure include bone tissues, such as the ribs and the spine, and soft tissues such as the lung or the stomach.

SUMMARY

As described above, the ES imaging according to the related art is completed by performing the two-shot imaging once. Therefore, the ES image acquired by the ES imaging according to the related art is a so-called still image. In contrast, the inventors have conducted a study on the continuous acquisition of a plurality of ES images. For example, the plurality of ES images are required for displaying a moving image according to a predetermined frame interval.

It is considered that the two-shot imaging is simply and continuously performed a plurality of times in order to continuously acquire a plurality of ES images. In a case in which the two-shot imaging is continuously performed a plurality of times, the amount of radiation naturally increases. However, there is a demand to reduce the amount of radiation as much as possible in consideration of the influence of the radiation on the subject.

An object of the technology of the present disclosure is to provide a radiography apparatus, a radiography apparatus operation method, and a radiography apparatus operation program that can reduce the amount of radiation in a case in which a plurality of energy subtraction images are continuously acquired, as compared to a case in which a two-shot imaging operation is continuously performed a plurality of times.

In order to achieve the object, according to the present disclosure, there is provided a radiography apparatus comprising: a radiation source that emits radiation; a radiation detector that detects the radiation transmitted through a subject and outputs a radiographic image of the subject; a radiation source control unit that performs control to direct the radiation source to emit first radiation with a first energy distribution and second radiation with a second energy distribution different from the first energy distribution in order to acquire an energy subtraction image in which a structure in the subject has been highlighted and performs radiation source control for performing a one-shot imaging operation, in which only one of the first radiation and the second radiation is emitted, at least once, for one two-shot imaging operation, in which the first radiation and the second radiation are continuously emitted, in a case in which an imaging mode continuously acquiring a plurality of the energy subtraction images is performed; and a detector control unit that performs detector control to direct the radiation detector to output a first radiographic image based on the first radiation and a second radiographic image based on the second radiation in a case in which the imaging mode is performed.

Preferably, the imaging mode is a moving image capture mode that continuously acquires a plurality of the energy subtraction images required for displaying a moving image according to a predetermined frame interval.

Preferably, the energy subtraction image corresponding to the two-shot imaging operation is generated on the basis of the first radiographic image and the second radiographic image output from the radiation detector in the two-shot imaging operation and the energy subtraction image corresponding to the one-shot imaging operation is generated on the basis of one of the first radiographic image and the second radiographic image output from the radiation detector in the one-shot imaging operation and the other of the first radiographic image and the second radiographic image output from the radiation detector in the two-shot imaging operation immediately before the one-shot imaging operation.

Preferably, in the imaging mode, the number of one-shot imaging operations is larger than the number of two-shot imaging operations.

Preferably, in the imaging mode, the two-shot imaging operation is performed once during a predetermined number of one-shot imaging operations.

Preferably, the radiography apparatus further comprises a detection unit that detects whether or not a body of the subject has moved. Preferably, in the imaging mode, the two-shot imaging operation is performed in a case in which the detection unit detects that the body of the subject has moved at a timing when the one-shot imaging operation is to be performed.

Preferably, the radiation source includes a radiation tube having a cold cathode. In this case, preferably, the cold cathode is a field emission type having an electron emission source that emits an electron beam using a field emission phenomenon.

Preferably, at least two radiation tubes of a first radiation tube that generates the first radiation and a second radiation tube that generates the second radiation are provided as the radiation tube.

Preferably, an intensity of the second radiation in the second energy distribution is lower than an intensity of the first radiation in the first energy distribution and the radiation source control unit directs the radiation source to emit only the second radiation in the one-shot imaging operation.

According to the present disclosure, there is provided a method for operating a radiography apparatus comprising a radiation source that emits radiation and a radiation detector that detects the radiation transmitted through a subject and outputs a radiographic image of the subject. The method comprises: a radiation source control step of performing control to direct the radiation source to emit first radiation with a first energy distribution and second radiation with a second energy distribution different from the first energy distribution in order to acquire an energy subtraction image in which a structure in the subject has been highlighted and performing radiation source control for performing a one-shot imaging operation, in which only one of the first radiation and the second radiation is emitted, at least once for one two-shot imaging operation, in which the first radiation and the second radiation are continuously emitted, in a case in which an imaging mode continuously acquiring a plurality of the energy subtraction images is performed; and a detector control step of performing detector control to direct the radiation detector to output a first radiographic image based on the first radiation and a second radiographic image based on the second radiation in a case in which the imaging mode is performed.

According to the present disclosure, there is provided a program for operating a radiography apparatus comprising a radiation source that emits radiation and a radiation detector that detects the radiation transmitted through a subject and outputs a radiographic image of the subject. The program causes a computer to function as: a radiation source control unit that performs control to direct the radiation source to emit first radiation with a first energy distribution and second radiation with a second energy distribution different from the first energy distribution in order to acquire an energy subtraction image in which a structure in the subject has been highlighted and performs radiation source control for performing a one-shot imaging operation, in which only one of the first radiation and the second radiation is emitted, at least once for one two-shot imaging operation, in which the first radiation and the second radiation are continuously emitted, in a case in which an imaging mode continuously acquiring a plurality of the energy subtraction images is performed; and a detector control unit that performs detector control to direct the radiation detector to output a first radiographic image based on the first radiation and a second radiographic image based on the second radiation in a case in which the imaging mode is performed.

According to the technology of the present disclosure, it is possible to provide a radiography apparatus, a radiography apparatus operation method, and a radiography apparatus operation program that can reduce the amount of radiation in a case in which a plurality of energy subtraction images are continuously acquired, as compared to a case in which a two-shot imaging operation is continuously performed a plurality of times.

BRIEF DESCRIPTION OF THE DRAWINGS

Exemplary embodiments according to the technique of the present disclosure will be described in detail based on the following figures, wherein:

FIG. 19 is a diagram illustrating an imaging mode in which a set of one two-shot imaging operation and three one-shot imaging operations is repeatedly performed;

DETAILED EMBODIMENTS

First Embodiment

Figure 1:
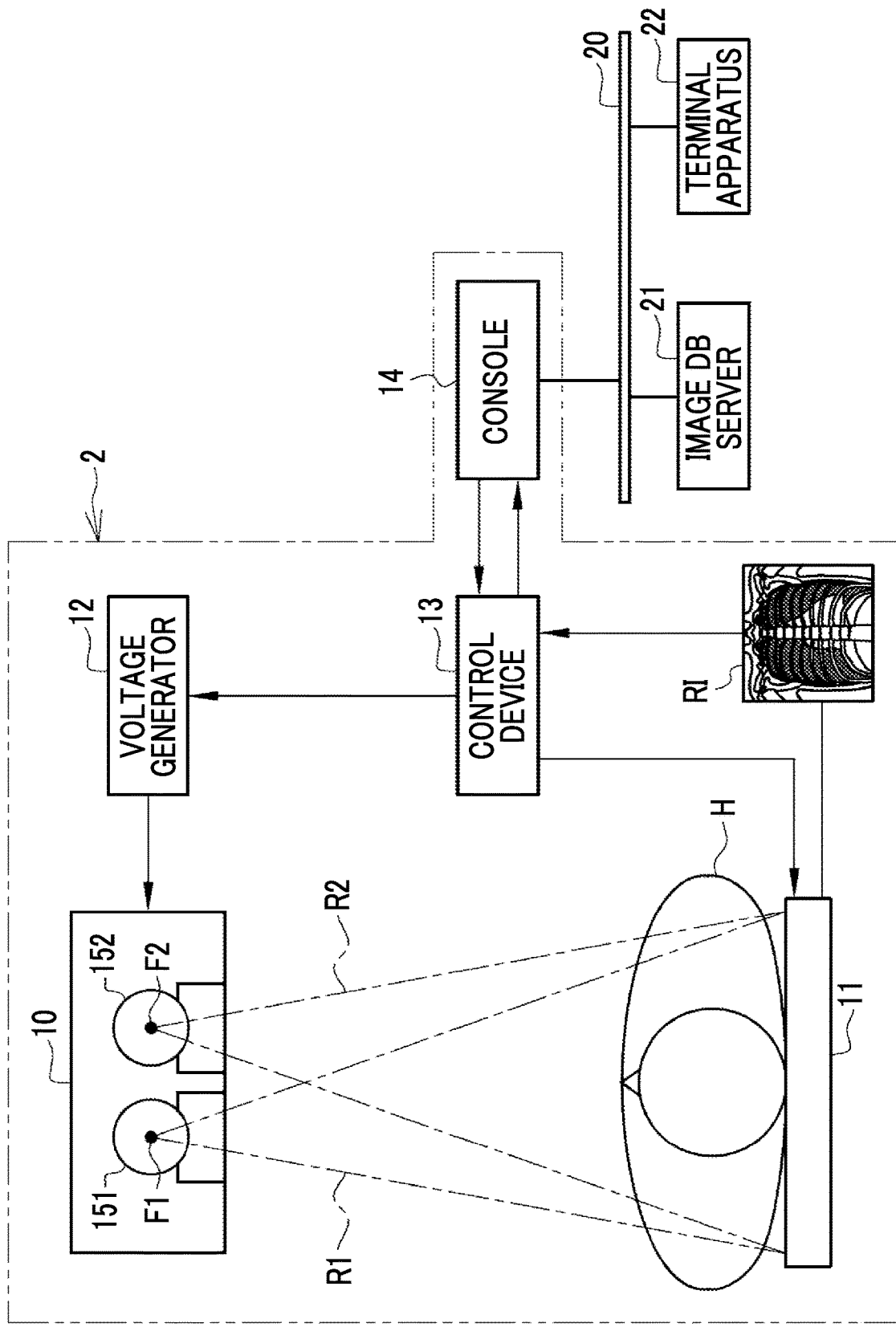
FIG. 1 is a diagram illustrating, for example, a radiography apparatus.

In FIG. 1, a radiography apparatus 2 comprises a radiation source 10, a radiation detector 11, a voltage generator 12, a control device 13, and a console 14. The radiation source 10, the radiation detector 11, the voltage generator 12, and the control device 13 are provided in, for example, a radiography room of a medical facility. The console 14 is provided in, for example, a control room adjacent to the radiography room. The radiography apparatus 2 is operated by a radiology technician.

The radiation source 10 includes a first radiation tube 151 and a second radiation tube 152. The first radiation tube 151 generates first radiation R1 from a first focus F1. The second radiation tube 152 generates second radiation R2 from a second focus F2. Hereinafter, in some cases, the first radiation tube 151 and the second radiation tube 152 are collectively referred to as a "radiation tube 15". Similarly, in some cases, the first focus F1 and the second focus F2 are collectively referred to as a "focus F" and the first radiation R1 and the second radiation R2 are collectively referred to as "radiation R". The radiation R is, for example, X-rays or γ-rays.

The radiation detector 11 detects the radiation R transmitted through a subject H and outputs a radiographic image RI of the subject H. The radiation detector 11 transmits the radiographic image RI to the control device 13. FIG. 1 illustrates an aspect in which a radiographic image of the chest of the subject H who lies in a supine position on a bed (not illustrated) is captured.

The radiation detector 11 has an imaging surface on which pixels converting the radiation R into electric signals are two-dimensionally arranged. The radiation detector 11 performs an accumulation operation that accumulates signal charge based on the radiation R in the pixel and a reading operation that reads the signal charge from the pixel and converts the signal charge into an electric signal. The radiation detector 11 is called a flat panel detector (FPD). The radiation detector 11 may be an indirect conversion type that includes a scintillator converting the radiation R into visible light and converts the visible light emitted from the scintillator into an electric signal or a direct conversion type that directly converts the radiation R into an electric signal. Hereinafter, in some cases, the electric signal is referred to as a "pixel value".

The voltage generator 12 generates a tube voltage to be applied to the radiation tube 15. The voltage generator 12 and the radiation tube 15 are connected to each other by a voltage cable (not illustrated). The tube voltage generated by the voltage generator 12 is supplied to the radiation tube 15 through the voltage cable.

The control device 13 controls the operation of the radiation source 10 through the voltage generator 12. The console 14 transmits the irradiation conditions of the radiation R to the control device 13. The control device 13 sets the irradiation conditions in the voltage generator 12. The irradiation conditions include a tube voltage applied to the radiation tube 15, a tube current, and the irradiation time of the radiation R. Instead of the tube current and the irradiation time, a tube current-irradiation time product (a so-called mAs value) may be used as the irradiation condition.

The radiology technician inputs a radiography start command to the control device 13 through an irradiation switch (not illustrated). In a case in which the start command is input, the control device 13 directs the radiation tube 15 to generate the radiation R under the set irradiation conditions.

The control device 13 also controls the operation of the radiation detector 11. The control device 13 directs the radiation detector 11 to perform the accumulation operation in synchronization with the timing when the radiation source 10 starts the emission of the radiation R. In addition, the control device 13 directs the radiation detector 11 to perform the reading operation in synchronization with the timing when the radiation source 10 ends the emission of the radiation R. Further, the control device 13 receives the radiographic image RI transmitted from the radiation detector 11. The control device 13 transmits the received radiographic image RI to the console 14.

The console 14 is, for example, a personal computer. The radiology technician inputs irradiation conditions to the console 14. The console 14 transmits the input irradiation conditions to the control device 13. In addition, the console 14 receives the radiographic image RI transmitted from the control device 13 and displays the radiographic image RI on a display.

The console 14 is connected to an image database (hereinafter, abbreviated to DB) server 21 through a network 20, such as a local area network (LAN), such that it can communicate with the image DB server 21. The image DB server 21 is, for example, a picture archiving and communication system (PACS) server, receives the radiographic image RI from the console 14, and accumulates and manages the radiographic image RI.

The terminal apparatus 22 is also connected to the network 20. The terminal apparatus 22 is, for example, a personal computer that is used by a doctor who makes a diagnosis based on the radiographic image RI. The terminal apparatus 22 receives the radiographic image RI from the image DB server 21 and displays the radiographic image RI on the display.

Figure 2:
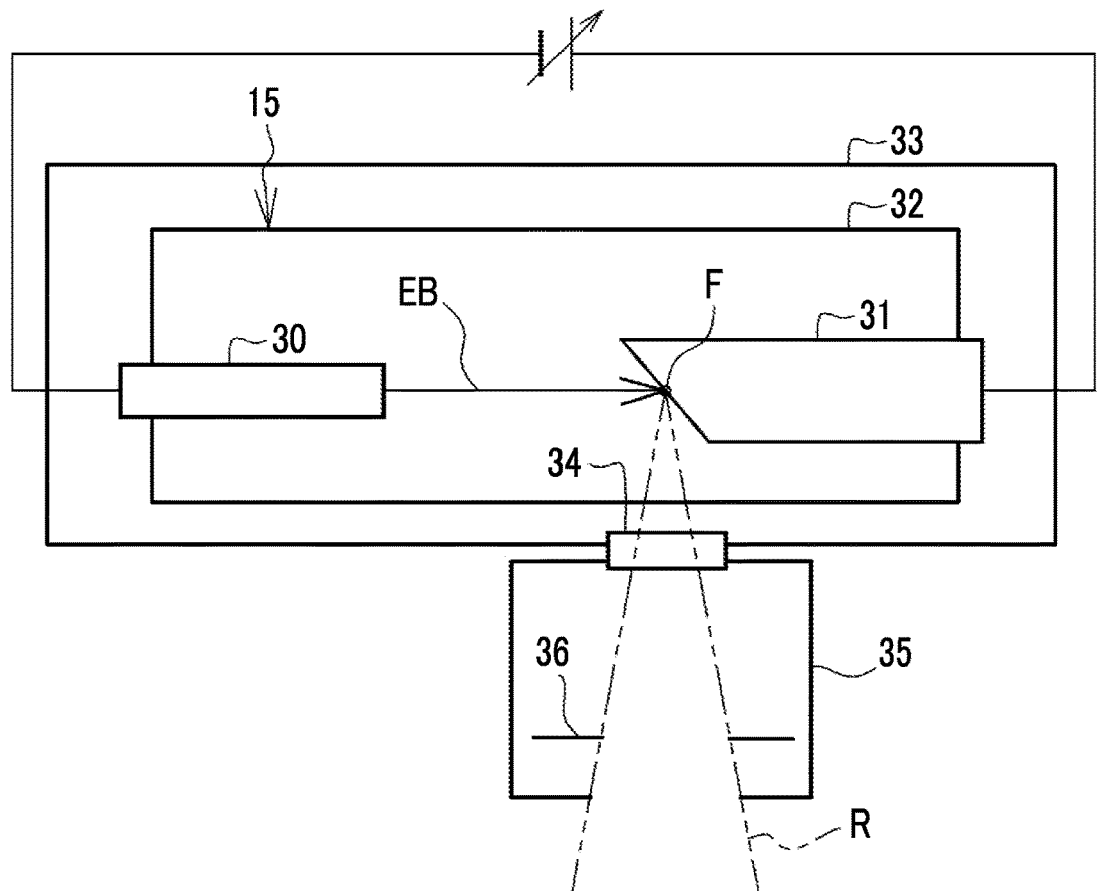
FIG. 2 is a diagram illustrating a radiation tube.

In FIG. 2, the radiation tube 15 includes a cathode 30 and an anode 31. The cathode 30 emits electrons. The electrons collide with the anode 31 and the anode 31 emits the radiation R. The cathode 30 and the anode 31 are accommodated in a vacuum glass tube 32 having a substantially cylindrical shape. The cathode 30 is a cold cathode. Specifically, the cathode 30 is a field emission type including an electron emission source that emits an electron beam EB to the anode 31, using a field emission phenomenon. The anode 31 is a fixed anode which is not rotated and whose position is fixed, unlike a rotating anode that is rotated by a rotation mechanism.

The voltage generator 12 applies a tube voltage between the cathode 30 and the anode 31. The electron beam EB is emitted from the cathode 30 to the anode 31 by the application of the tube voltage. Then, the radiation R is emitted from the focus F which is a point of the anode 31 where the electron beam EB collides.

The radiation tube 15 is accommodated in a housing 33. The housing 33 is provided with a radiation transmission window 34 that transmits the radiation R. The radiation R emitted from the anode 31 is emitted to the outside of the housing 33 through the radiation transmission window 34. In addition, the housing 33 is filled with insulating oil.

An irradiation field limiter 35 is provided in the radiation transmission window 34. The irradiation field limiter 35 is also called a collimator and sets the irradiation field of the radiation R in an imaging surface of the radiation detector 11. Specifically, the irradiation field limiter 35 includes a plurality of shielding plates 36 which are made of, for example, lead and shield the radiation R transmitted through the radiation transmission window 34. The shielding plates 36 are moved to change the size of, for example, a rectangular irradiation opening defined by the shielding plates 36, thereby setting the irradiation field of the radiation R.

Figure 3:
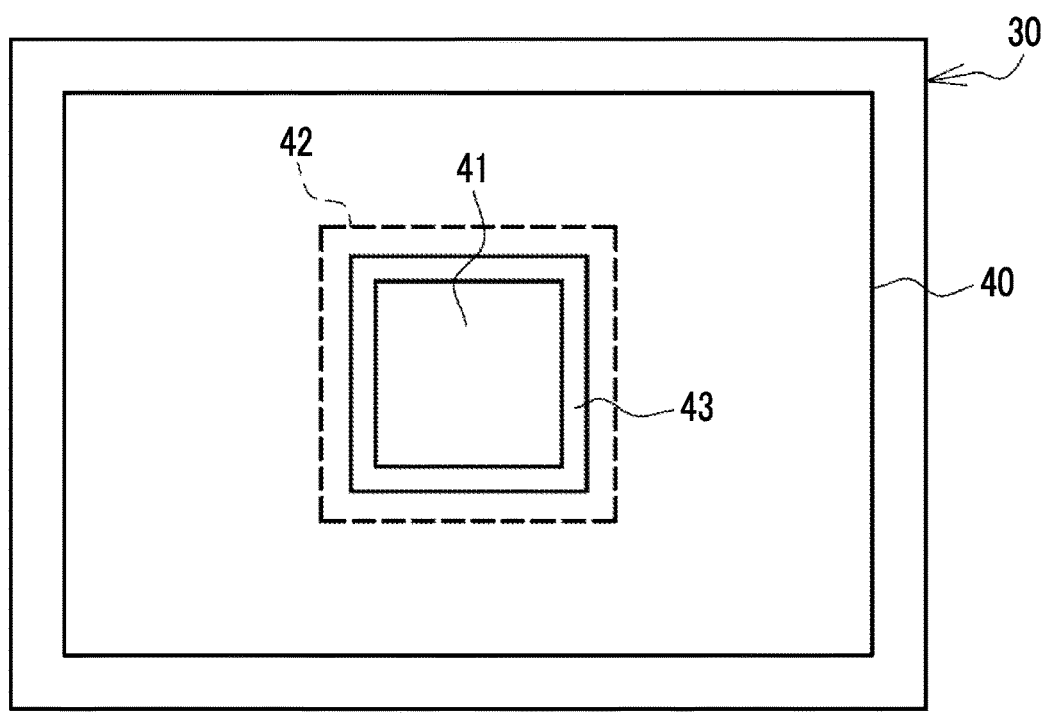
FIG. 3 is a diagram illustrating a cathode.

In FIG. 3, the cathode 30 has a structure in which an emitter electrode 41 and a gate electrode 42 are provided on a semiconductor substrate 40. The semiconductor substrate

40 is made of, for example, crystallized silicon. The emitter electrode 41 is, for example, a cone-shaped carbon nanotube. The emitter electrode 41 is connected to the gate electrode 42. The emitter electrode 41 functions as an emission area of the electron beam EB. That is, the emitter electrode 41 is an example of an "electron emission source" according to the technology of the present disclosure.

A focusing electrode 43 is provided around the emitter electrode 41. In a case in which a focusing voltage is applied to the focusing electrode 43, the electron beam EB emitted from the emitter electrode 41 is accelerated toward the anode 31 and is focused.

Figure 4:
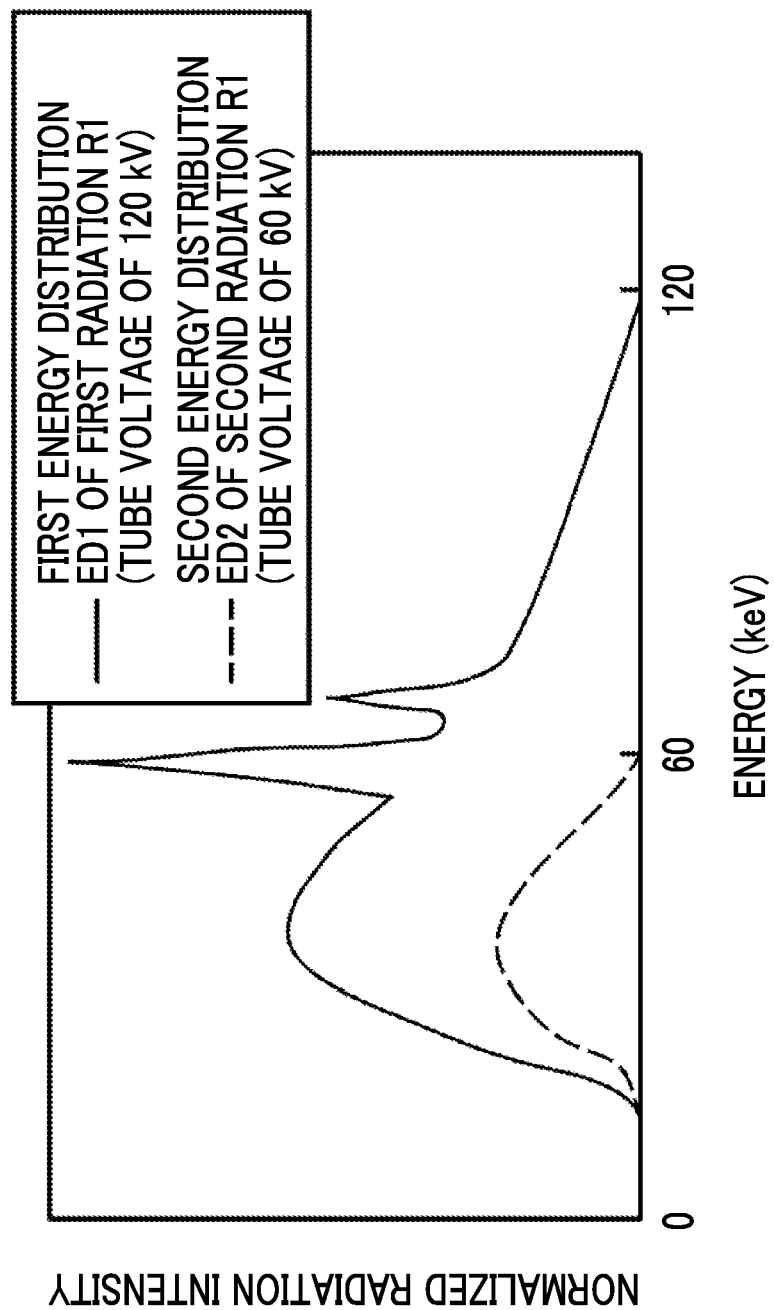
FIG. 4 is a graph illustrating a first energy distribution of first radiation and a second energy distribution of second radiation.

In FIG. 4, the first radiation R1 generated from the first radiation tube 151 has a first energy distribution ED1 represented by a solid line. In contrast, the second radiation R2 generated from the second radiation tube 152 has a second energy distribution ED2 represented by a dashed line. The first radiation R1 is generated by setting a tube voltage higher than the second radiation R2, for example, a tube voltage of 120 kV. The second radiation R2 is generated by setting a tube voltage lower than the first radiation R1, for example, a tube voltage of 60 kV. The intensity of the second radiation R2 in the second energy distribution ED2 is lower than the intensity of the first radiation R1 in the first energy distribution ED1 due to the difference between the tube voltage levels. In short, the second radiation R2 has lower energy than the first radiation R1. Hereinafter, in some cases, the first energy distribution ED1 and the second energy distribution ED2 are collectively referred to as an "energy distribution ED".

Figure 5:
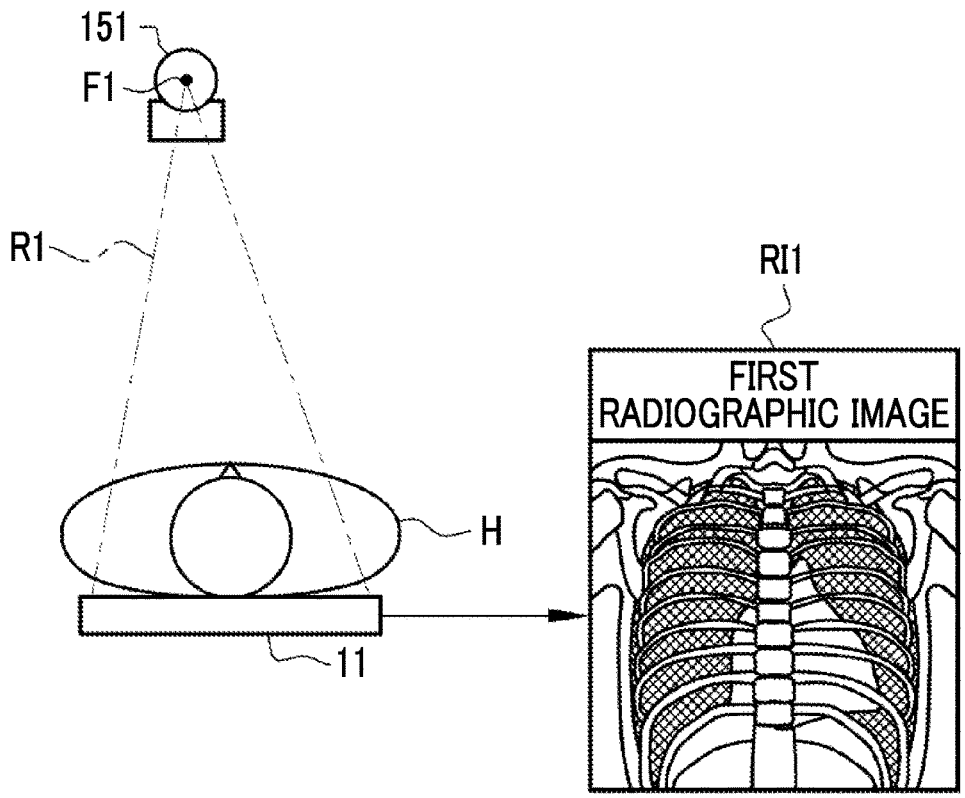
FIG. 5 is a diagram illustrating an aspect in which a first radiation tube generates the first radiation and a radiation detector outputs a first radiographic image based on the first radiation transmitted through a subject.
Figure 6:
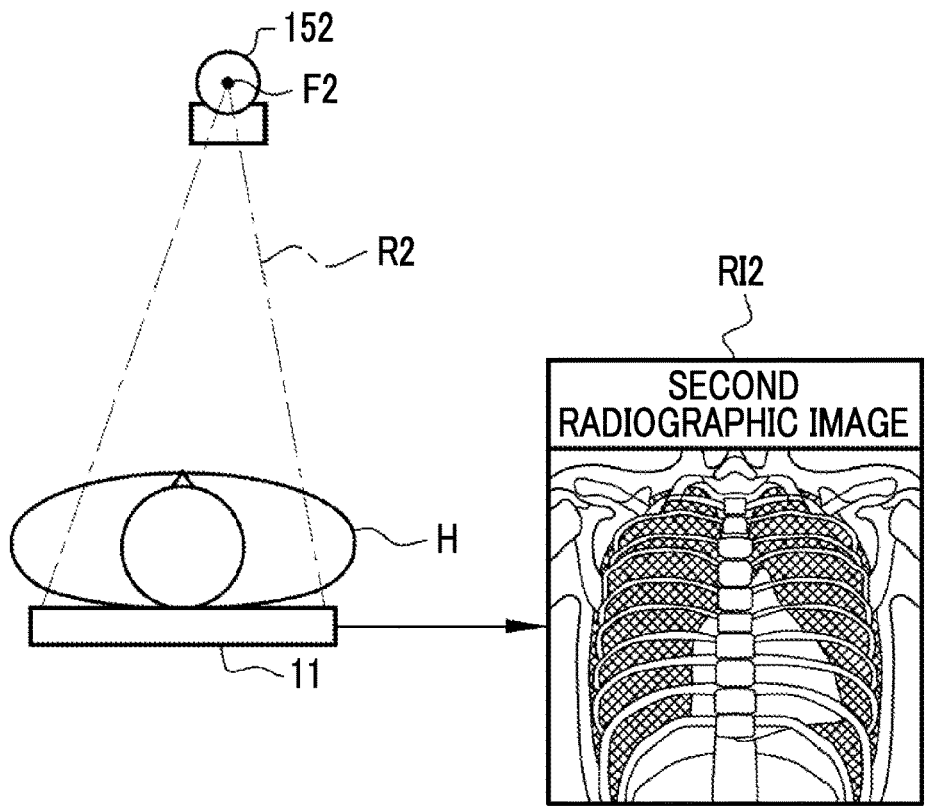
FIG. 6 is a diagram illustrating an aspect in which a second radiation tube generates the second radiation and the radiation detector outputs a second radiographic image based on the second radiation transmitted through the subject.

FIG. 5 illustrates an aspect in which the first radiation tube 151 generates the first radiation R1 and the radiation detector 11 outputs a first radiographic image RI1 based on the first radiation R1 transmitted through the subject H. In contrast, FIG. 6 illustrates an aspect in which the second radiation tube 152 generates the second radiation R2 and the radiation detector 11 outputs a second radiographic image RI2 based on the second radiation R2 transmitted through the subject H. As such, the radiography apparatus 2 can perform ES imaging in which the radiation source 10 continuously emits the first radiation R1 and the second radiation R2 having different energy distributions ED as illustrated in FIG. 4 and the radiation detector 11 outputs the first radiographic image RI1 and the second radiographic image RI2.

The first radiographic image RI1 and the second radiographic image RI2 include both bone tissues, such as the ribs and the spine, and soft tissues, such as the lung and the stomach. However, the energy levels of the radiation R that are easily absorbed by the bone tissues and the soft tissues are different from each other. Therefore, the bone tissue included in the first radiographic image RI1 and the bone tissue included in the second radiographic image RI2 have different pixel values. In addition, the soft tissue included in the first radiographic image RI1 and the soft tissue included in the second radiographic image RI2 have different pixel values.

Figure 7:
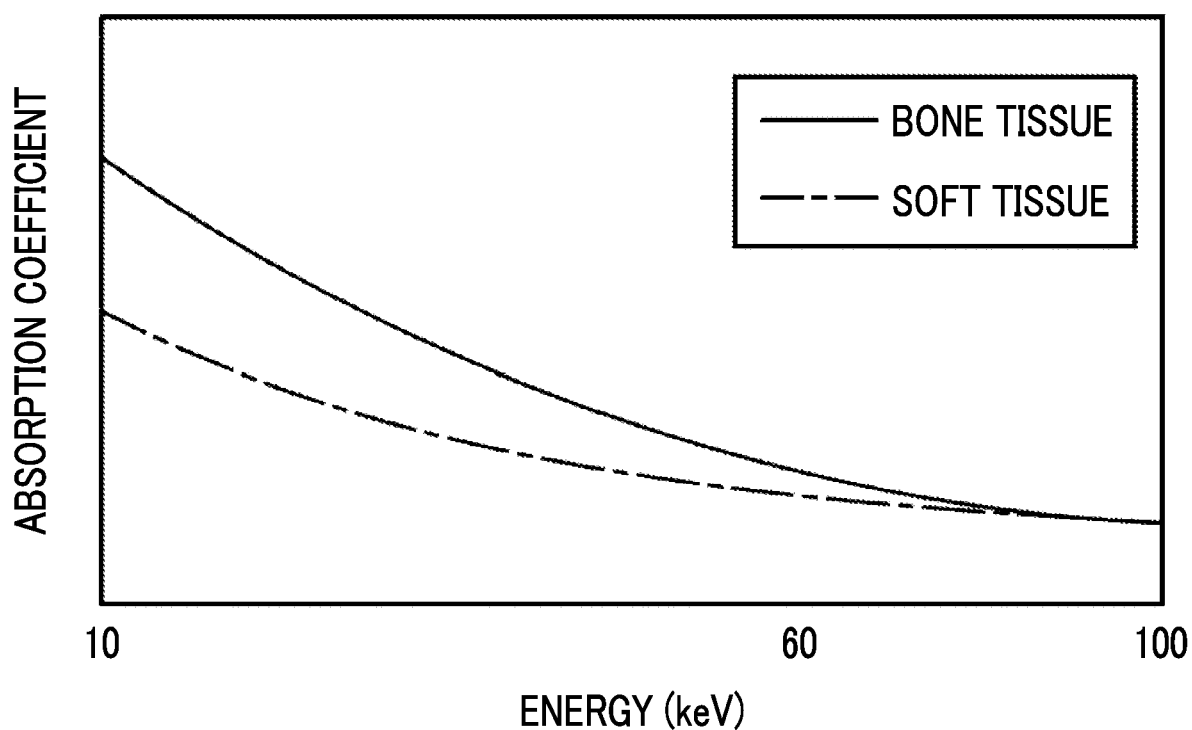
FIG. 7 is a graph illustrating absorption coefficients of a bone tissue and a soft tissue for the energy of radiation.

Specifically, as illustrated in FIG. 7, the difference between an absorption coefficient of the bone tissue and an absorption coefficient of the soft tissue for the radiation R with relatively high energy is small. On the other hand, the difference between an absorption coefficient of the bone tissue and an absorption coefficient of the soft tissue for the radiation R with relatively low energy is large. The radiation R with relatively high energy is the first radiation R1 and the radiation R with relatively low energy is the second radiation R2. Therefore, in the first radiographic image RI1, the ratio of the pixel value of the bone tissue to the pixel value of the soft tissue is low. In contrast, in the second radiographic image RI2, the ratio of the pixel value of the bone tissue to the pixel value of the soft tissue is high.

Figure 8:
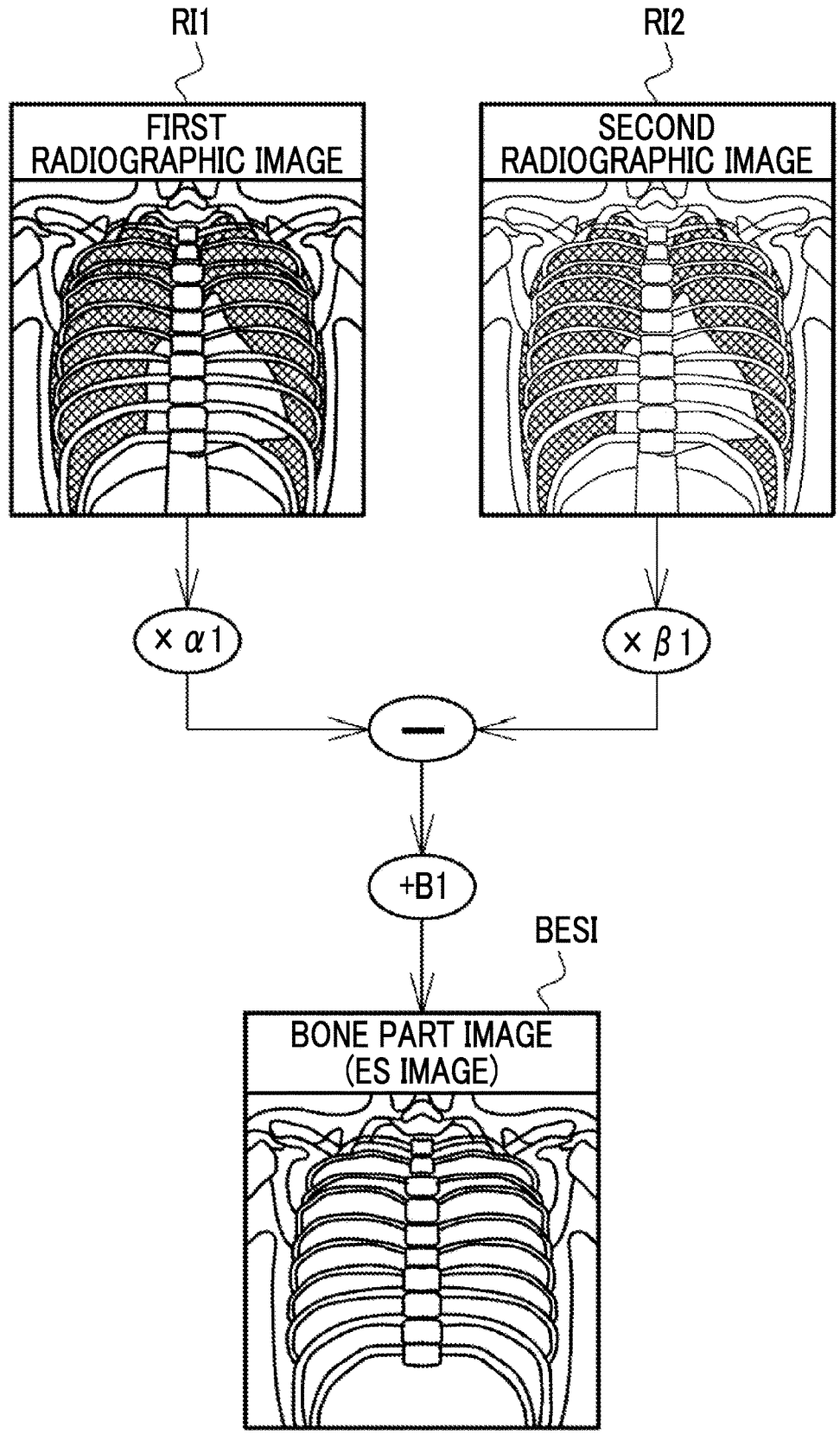
FIG. 8 is a diagram illustrating an aspect in which a bone part image is generated.
Figure 9:
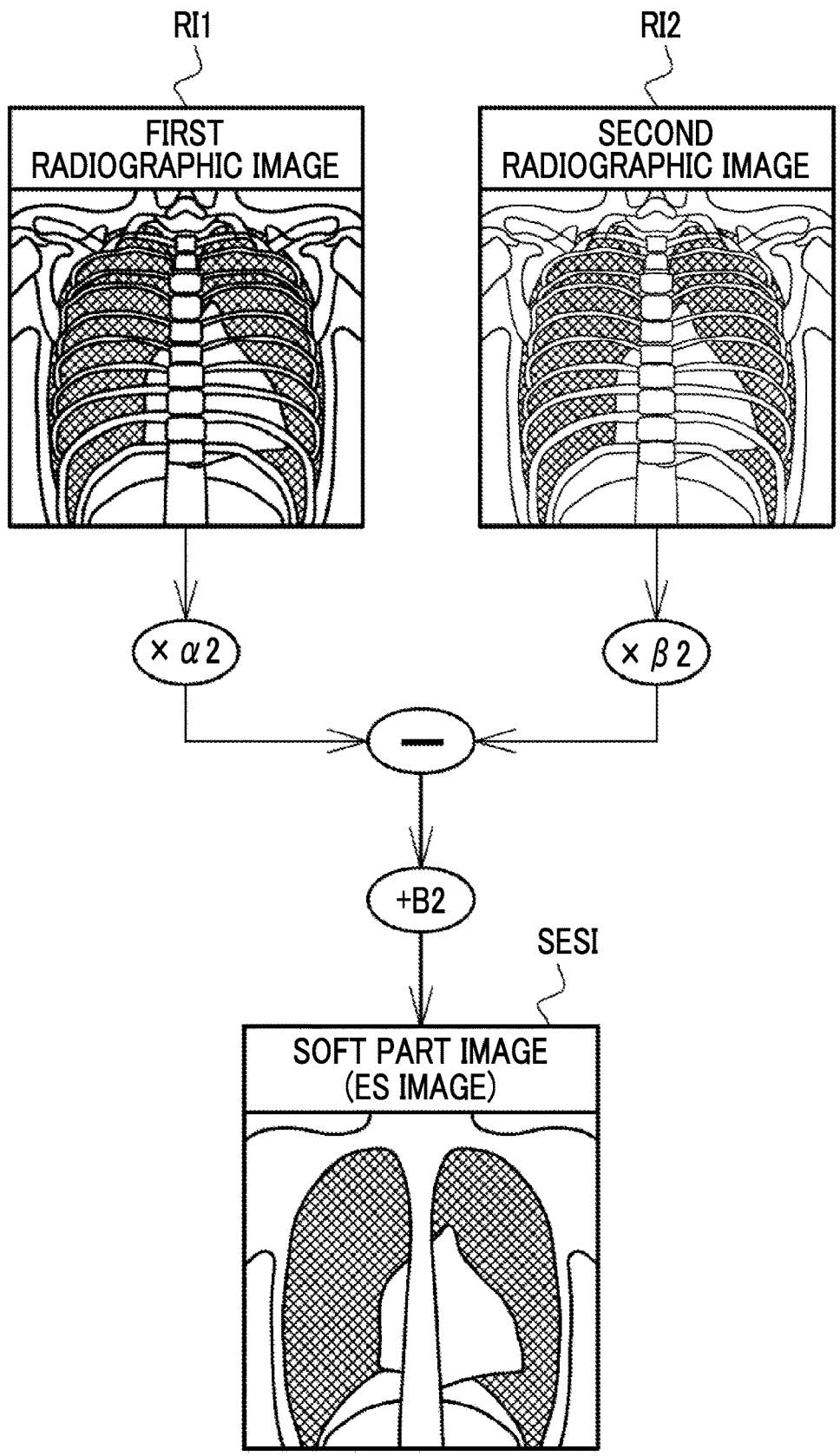
FIG. 9 is a diagram illustrating an aspect in which a soft part image is generated.

FIGS. 8 and 9 illustrate aspects in which an ES image in which a structure in the subject H has been highlighted is generated on the basis of the first radiographic image RI1 and the second radiographic image RI2, using the difference between the absorption coefficients of the bone tissue and the soft tissue for the radiation R illustrated in FIG. 7. FIG. 8 illustrates an aspect in which a bone part image BESI in which the bone tissue has been highlighted is generated. In contrast, FIG. 9 illustrates an aspect in which a soft part image SESI in which the soft tissue has been highlighted is generated. Hereinafter, in some cases, the bone part image BESI and the soft part image SESI are collectively referred to as an "ES image ESI".

In FIG. 8, the bone part image BESI is generated by performing calculation represented by the following Expression (1):

$$BESI = RI1 \times \sigma 1 - RI2 \times \beta 1 + B1 \qquad (1).$$

In addition, $\sigma 1$ and $\beta 1$ are weighting coefficients and B1 is a bias value.

The weighting coefficients $\sigma 1$ and $\beta 1$ are adjusted to values at which the pixel values of the soft tissues in the first radiographic image RI1 and the second radiographic image RI2 are matched with each other. Therefore, in a case in which the pixel value of the first radiographic image RI1 is multiplied by the weighting coefficient $\sigma 1$ and the pixel value of the second radiographic image RI2 is multiplied by the weighting coefficient $\beta 1$ and the difference between the pixel values is calculated, it is possible to generate the bone part image BESI in which the soft tissues have been removed and only the bone tissues have been drawn.

In FIG. 9, the soft part image SESI is generated by performing calculation represented by the following Expression (2):

$$SESI = RI1 \times \sigma 2 - RI2 \times \beta 2 + B2 \qquad (2).$$

In addition, $\sigma 2$ and $\beta 2$ are weighting coefficient and B2 is a bias value.

Similarly to the weighting coefficients $\sigma 1$ and $\beta 1$, the weighting coefficients $\sigma 2$ and $\beta 2$ are adjusted to values at which the pixel values of the bone tissues in the first radiographic image RI1 and the second radiographic image RI2 are matched with each other. Therefore, in a case in which the pixel value of the first radiographic image RI1 is multiplied by the weighting coefficient $\sigma 2$ and the pixel value of the second radiographic image RI2 is multiplied by the weighting coefficient $\beta 2$ and the difference between the pixel values is calculated, it is possible to generate the soft part image SESI in which the bone tissues have been removed and only the soft tissues have been drawn.

The ES image ESI is generated by, for example, the console 14. The console 14 transmits the generated ES image ESI and the first and second radiographic images RI1 and RI2 which are the generation sources of the ES image ESI to the image DB server 21 in association with each other. In addition, the control device 13, the image DB server 21, or the terminal apparatus 22 may generate the ES image ESI.

Figure 10:
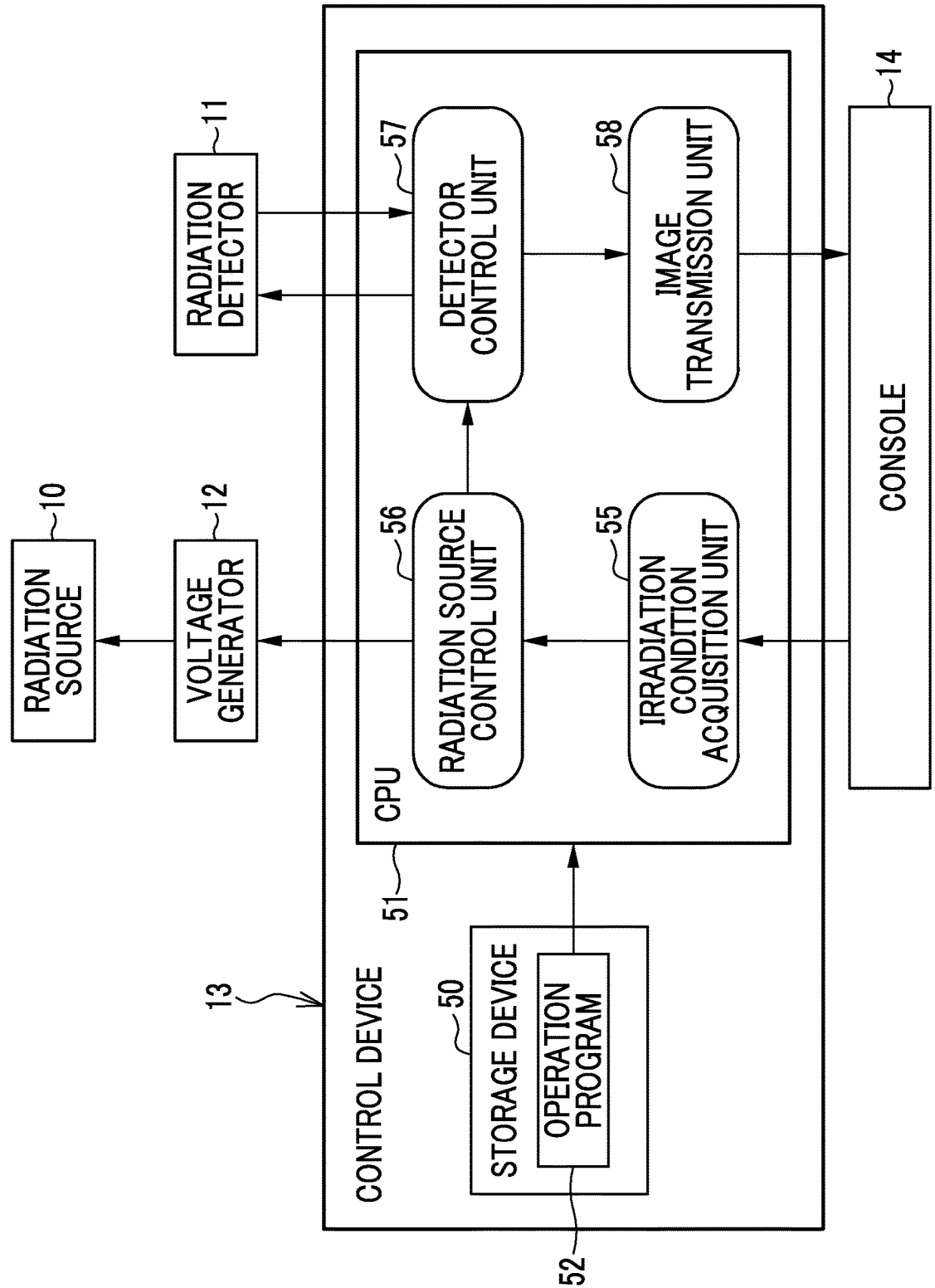
FIG. 10 is a block diagram illustrating a CPU of a control device.

As illustrated in FIG. 10, the control device 13 comprises a storage device 50 and a central processing unit (CPU) 51. The storage device 50 is, for example, a hard disk drive. The storage device 50 stores an operation program 52. The operation program 52 is an example of a "radiography apparatus operation program" according to the technology of the present disclosure. In a case in which the operation program 52 is started, the CPU 51 functions as an irradiation condition acquisition unit 55, a radiation source control unit 56, a detector control unit 57, and an image transmission unit 58 in cooperation with, for example, a memory (not illustrated).

The irradiation condition acquisition unit 55 acquires the irradiation conditions transmitted from the console 14. The irradiation condition acquisition unit 55 outputs the acquired irradiation conditions to the radiation source control unit 56.

The radiation source control unit 56 controls the operation of the radiation source 10. The radiation source control unit 56 sets the irradiation conditions from the irradiation condition acquisition unit 55 in the voltage generator 12. In a case in which a radiography start command is input, the radiation source control unit 56 directs the radiation tube 15 to generate the radiation R under the set irradiation conditions. The radiation source control unit 56 outputs an irradiation start notification signal for notifying the start of the emission of the radiation R and an irradiation end notification signal for notifying the end of the emission of the radiation R to the detector control unit 57. In addition, as illustrated in FIGS. 5 and 6, the radiation source control unit 56 performs control to direct the radiation source 10 to emit the first radiation R1 and the second radiation R2 in order to acquire the ES image ESI.

The detector control unit 57 controls the operation of the radiation detector 11. The detector control unit 57 directs the radiation detector 11 to perform the accumulation operation in response to the irradiation start notification signal from the radiation source control unit 56. In addition, the detector control unit 57 directs the radiation detector 11 to perform the reading operation in response to the irradiation end notification signal from the radiation source control unit 56. Then, the detector control unit 57 directs the radiation detector 11 to output the radiographic image RI. The detector control unit 57 receives the radiographic image RI transmitted from the radiation detector 11 and outputs the received radiographic image RI to the image transmission unit 58. Further, as illustrated in FIGS. 5 and 6, the detector control unit 57 directs the radiation detector 11 to output the first radiographic image RI1 based on the first radiation R1 and the second radiographic image RI2 based on the second radiation R2.

The image transmission unit 58 transmits the radiographic image RI from the detector control unit 57 to the console 14.

Figure 11:
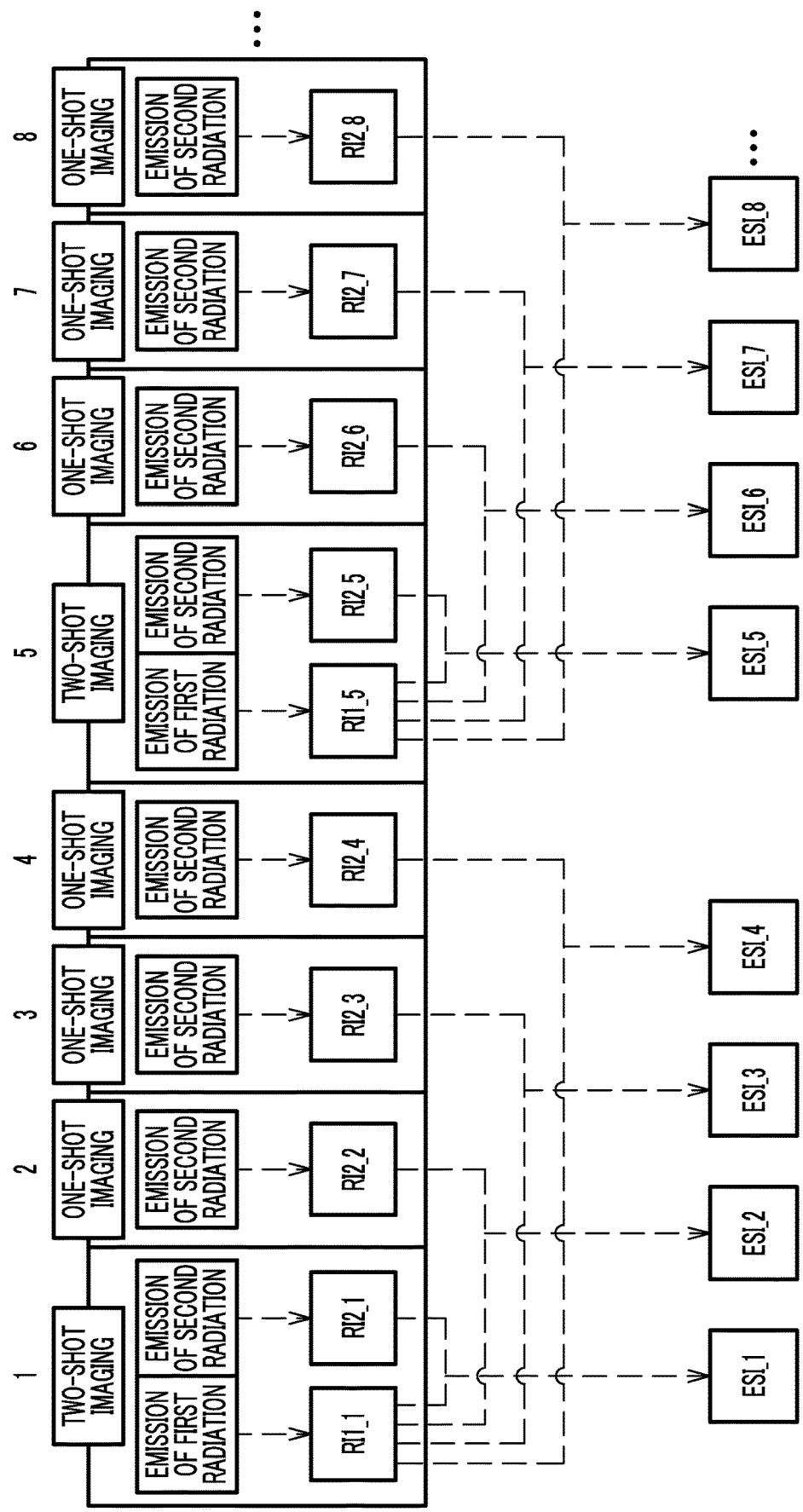
FIG. 11 is a diagram illustrating an imaging mode that continuously acquires a plurality of ES images.

The radiography apparatus 2 performs an imaging mode that continuously acquires a plurality of ES images ESI. In a case in which the imaging mode is performed, the radiation source control unit 56 performs radiation source control for performing a one-shot imaging operation at least once for one two-shot imaging operation as illustrated in FIG. 11. In addition, in a case in which the imaging mode is performed, the detector control unit 57 performs detector control to direct the radiation detector 11 to output the first radiographic image RI1 based on the first radiation R1 and the second radiographic image RI2 based on the second radiation R2.

Here, the two-shot imaging operation indicates radiography in which the first radiation R1 and the second radiation R2 are continuously emitted and the radiation detector 11 outputs the first radiographic image RI1 and the second radiographic image RI2. In FIG. 11, frame 1, frame 5, . . . correspond to the two-shot imaging operation.

In contrast, the one-shot imaging operation indicates radiography in which only one of the first radiation R1 and the second radiation R2 is emitted and the radiation detector 11 outputs only one of the first radiographic image RI1 and the second radiographic image RI2. In FIG. 11, frames 2 to 4, frames 6 to 8, . . . other than frame 1, frame 5, . . . corresponding to the two-shot imaging operation correspond to the one-shot imaging operation.

In FIG. 11, only the second radiation R2 is emitted in the one-shot imaging operation. That is, the second radiation R2 is an example of "one of the first radiation and the second radiation" according to the technology of the present disclosure. In this case, in the one-shot imaging operation, the radiation detector 11 outputs only the second radiographic image RI2. That is, the second radiographic image RI2 is an example of "one of the first radiographic image and the second radiographic image" according to the technology of the present disclosure. Conversely, the first radiographic image RI1 is an example of "the other of the first radiographic image and the second radiographic image" according to the technology of the present disclosure.

In FIG. 11, in a case in which four consecutive frames are viewed, the number of two-shot imaging operations is 1 and the number of one-shot imaging operations is 3. That is, the number of one-shot imaging operations is larger than the number of two-shot imaging operations. Further, in FIG. 11, one two-shot imaging operation is performed during three one-shot imaging operations. That is, one two-shot imaging operation is performed during a predetermined number of one-shot imaging operations. The predetermined number of imaging operations is not limited to 3 illustrated in FIG. 11, but may be 2 or 3 or more. Further, for example, a configuration in which the radiology technician can change the setting of the predetermined number of imaging operations may be used.

The ES image ESI corresponding to the two-shot imaging operation is generated on the basis of the first radiographic image RI1 and the second radiographic image RI2 output from the radiation detector 11 in the two-shot imaging operation. For example, an ES image ESI_1 of frame 1 is generated on the basis of a first radiographic image RI1_1 and a second radiographic image RI2_1.

In contrast, the ES image ESI corresponding to the one-shot imaging operation is generated on the basis of one of the first radiographic image RI1 and the second radiographic image RI2 output from the radiation detector 11 in the one-shot imaging operation and the other of the first radiographic image RI1 and the second radiographic image RI2 output in the two-shot imaging operation immediately before the one-shot imaging operation.

In FIG. 11, as described above, "one of the first radiographic image RI1 and the second radiographic image RI2" is the second radiographic image RI2 and "the other of the first radiographic image RI1 and the second radiographic image RI2" is the first radiographic image RI1. Therefore, for example, an ES image ESI_2 of frame 2 is generated on the basis of the first radiographic image RI1_1 of frame 1 in the most recent two-shot imaging operation and the second radiographic image RI2_2. For example, an ES image ESI_8 of frame 8 is generated on the basis of a first radiographic image RI1_5 of frame 5 in the most recent two-shot imaging operation and a second radiographic image RI2_8.

Figure 12:
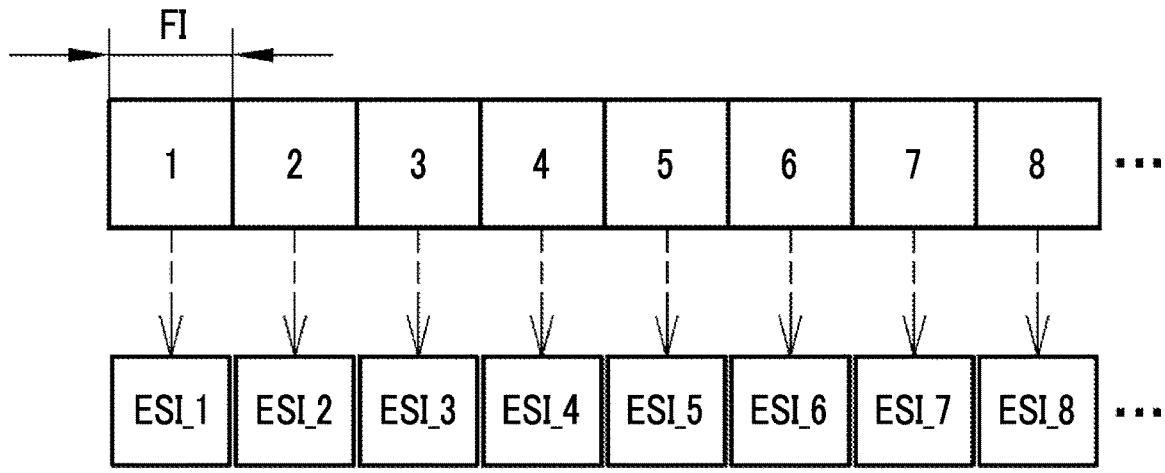
FIG. 12 is a diagram illustrating an aspect in which a plurality of ES images are displayed as a moving image according to a predetermined frame interval.

A plurality of ES images ESI_1, ESI_2, ESI_3, . . . generated in frames 1, 2, 3, . . . as illustrated in FIG. 11 are continuously acquired for the display of a moving image according to a predetermined frame interval FI as illustrated in FIG. 12. That is, the imaging mode is a moving image capture mode that continuously acquires a plurality of ES images ESI required for the display of a moving image according to the frame interval FI. The frame interval FI is, for example, about 0.03 seconds (30 frames/second in frame rate).

Figure 13:
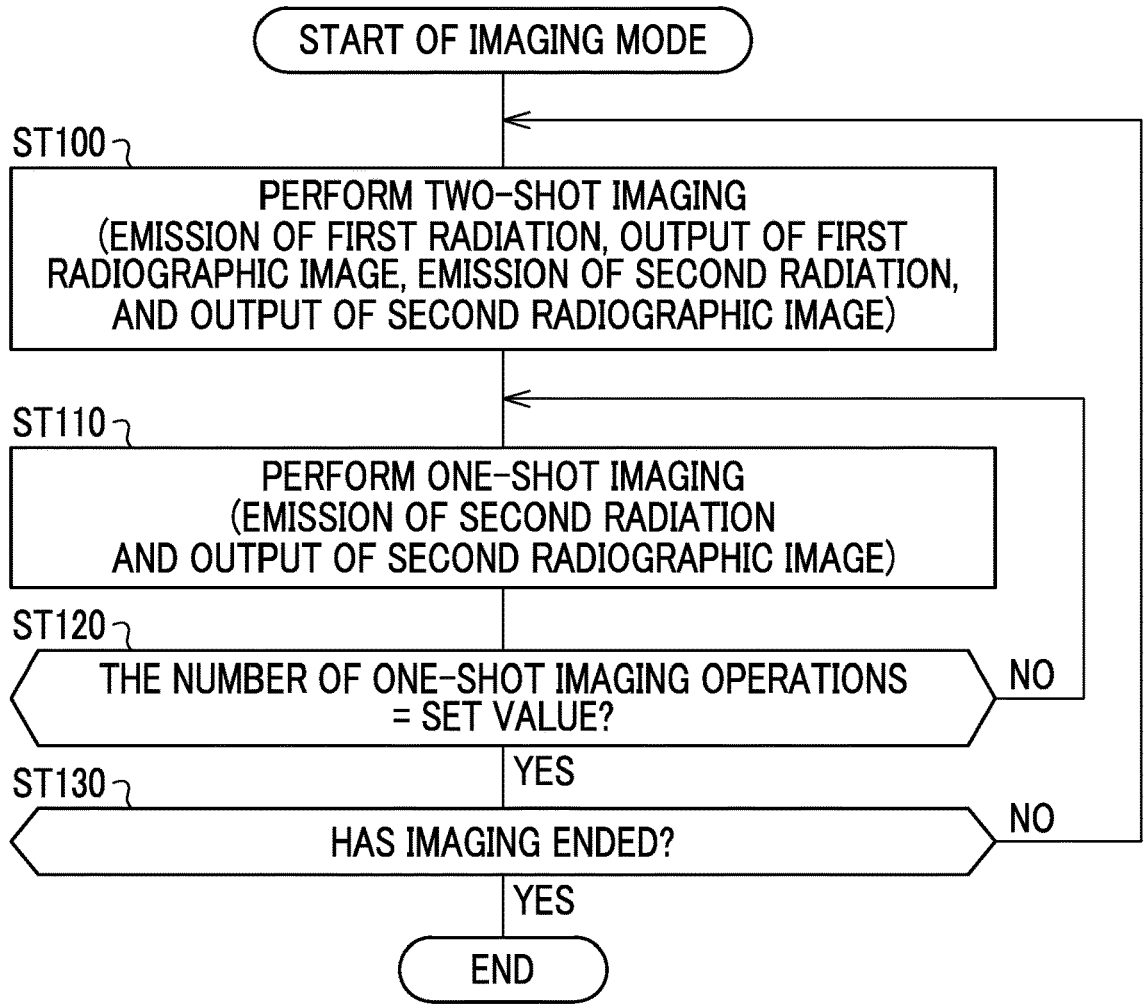
FIG. 13 is a flowchart illustrating a process procedure of the radiography apparatus.

Next, the operation of the above-mentioned configuration will be described with reference to a flowchart illustrated in FIG. 13. A radiography procedure of the radiography apparatus 2 starts from an imaging preparation operation. The imaging preparation operation is performed by the radiology technician. The imaging preparation operation includes, specifically, an operation related to the positioning of the subject H and an operation of inputting irradiation conditions to the console 14. After the imaging preparation operation ends, the radiology technician inputs a radiography start command.

In the control device 13, the irradiation condition acquisition unit 55 acquires the irradiation conditions from the console 14. The irradiation conditions are output from the irradiation condition acquisition unit 55 to the radiation source control unit 56 and are set in the voltage generator 12 by the radiation source control unit 56.

In a case in which the radiography start command is input, first, a two-shot imaging operation is performed as illustrated in FIG. 11 (Step ST100). Specifically, the radiation source control unit 56 directs the radiation source 10 to continuously emit the first radiation R1 and the second radiation R2. In addition, the detector control unit 57 directs the radiation detector 11 to output the first radiographic image RI1 and the second radiographic image RI2.

Then, the one-shot imaging operation is performed (Step ST110). Specifically, the radiation source control unit 56 directs the radiation source 10 to emit the second radiation R2. In addition, the detector control unit 57 directs the radiation detector 11 to output the second radiographic image RI2. Step ST100 is an example of a "radiation source control step" and a "detector control step" according to the technology of the present disclosure. Step ST110 is also an example of the "radiation source control step" and the "detector control step" according to the technology of the present disclosure.

The one-shot imaging operation is repeated until the number of one-shot imaging operations reaches a set value (3 in the example illustrated in FIG. 11) (NO in Step ST120). After the one-shot imaging operation is repeated a set number of times, the two-shot imaging operation is performed again (YES in Step ST120 and No in Step ST130). The imaging mode in which one two-shot imaging operation and a set number of one-shot imaging operations form a set is continued until the imaging ends (YES in Step ST130).

The radiographic image RI output from the radiation detector 11 is output from the detector control unit 57 to the image transmission unit 58. The radiographic image RI is transmitted to the console 14 by the image transmission unit 58.

In the console 14, as illustrated in FIG. 8, FIG. 9, and FIG. 11, a plurality of ES images ESI are generated on the basis of the first radiographic image RI1 and the second radiographic image RI2. As illustrated in FIG. 12, the plurality of generated ES images ESI are displayed as a moving image according to a predetermined frame interval FI in, for example, the console 14 or the terminal apparatus 22 and are provided for doctor's browsing.

As described above, in a case in which the imaging mode that continuously acquires a plurality of ES images ESI is performed, the radiation source control unit 56 performs radiation source control for performing at least one one-shot imaging operation in which only one of the first radiation R1 and the second radiation R2 is emitted for one two-shot imaging operation in which the first radiation R1 and the second radiation R2 are continuously emitted. In addition, in a case in which the imaging mode is performed, the detector control unit 57 performs detector control for directing the radiation detector 11 to output the first radiographic image RI1 based on the first radiation R1 and the second radiographic image RI2 based on the second radiation R2. Therefore, the amount of radiation R can be less than that in a case in which the two-shot imaging operation is continuously performed a plurality of times. As a result, it is possible to reduce the amount of radiation exposure of the subject H. Further, the load on the radiation tube 15 and the radiation detector 11 can be less than that in a case in which the two-shot imaging operation is continuously performed a plurality of times.

As illustrated in FIG. 12, the imaging mode is a moving image capture mode that continuously acquires a plurality of ES images ESI required for displaying a moving image according to the predetermined frame interval FI. Therefore, it is possible to provide a moving image of the ES images ESI for doctor's browsing and to develop new possibilities for medical diagnosis using the ES images ESI.

As illustrated in FIG. 11, the ES image ESI corresponding to the two-shot imaging operation is generated on the basis of the first radiographic image RI1 and the second radiographic image RI2 output from the radiation detector 11 in the two-shot imaging operation. In contrast, the ES image ESI corresponding to the one-shot imaging operation is generated on the basis of one of the first radiographic image RI1 and the second radiographic image RI2 output from the radiation detector 11 in the one-shot imaging operation and the other of the first radiographic image RI1 and the second radiographic image RI2 output in the two-shot imaging operation immediately before the one-shot imaging operation. Therefore, it is possible to continuously acquire a plurality of ES images ESI without continuously performing the two-shot imaging operation a plurality of times. Further, in a case in which the ES image ESI corresponding to the one-shot imaging operation is generated, the other of the first radiographic image RI1 and the second radiographic image RI2 output in the most recent two-shot imaging operation is reused. Therefore, it is possible to reduce the load on the process of generating the ES images ESI.

As illustrated in FIG. 11, in the imaging mode, the number of one-shot imaging operations is larger than the number of two-shot imaging operations. Therefore, it is possible to further reduce the amount of radiation R, as compared to a case in which the number of two-shot imaging operations is equal to or larger than the number of one-shot imaging operations.

As illustrated in FIG. 11, in the imaging mode, one two-shot imaging operation is performed during a predetermined number of one-shot imaging operations. Therefore, the two-shot imaging operation and the one-shot imaging operation may be regularly performed. It is possible to simply perform the radiation source control and the detector control.

In addition, as illustrated in FIG. 11, the radiation source control unit 56 performs control such that only the second radiation R2 with low intensity is emitted in the one-shot imaging operation. Therefore, it is possible to further reduce the amount of radiation R, as compared to a case in which only the first radiation R1 with high intensity is emitted. In a case in which only the first radiation R1 with high intensity is emitted, there is a high possibility that a residual image will be generated in the radiation detector 11 after the detection of the first radiographic image RI1. However, in a case in which the second radiation R2 with low intensity is used, there is a low possibility that a residual image will be generated. Therefore, it is possible to suppress the quality degradation of the second radiographic image RI2 due to the residual image and thus to suppress the quality degradation of the ES image ESI.

As illustrated in FIGS. 2 and 3, the radiation tube 15 has the cathode 30 which is a cold cathode. The cold cathode generates the amount of heat that is much less than that a cathode with a filament structure which emits thermal electrons. Therefore, a heat radiation structure is not required and it is possible to reduce the size of the radiation tube 15. Specifically, it is possible to reduce the diameter of the radiation tube 15 to, for example, about 50 mm or less. Therefore, this configuration can contribute to reducing the size of the radiation source 10.

In a case in which two radiation tubes 15, that is, the first radiation tube 151 and the second radiation tube 152 are used as in this embodiment and the two radiation tubes 15 have the cathodes 30 which are cold cathodes, the first radiation tube 151 and the second radiation tube 152 can be arranged close to each other since they are small. In other words, it is possible to reduce the distance between the first focus F1 of the first radiation R1 and the second focus F2 of the second radiation R2. Therefore, the deviation of the irradiation angles of the first radiation R1 and the second radiation R2 with respect to the imaging surface of the radiation detector 11 which affects the quality of the ES image ESI is reduced. As a result, it is possible to acquire the ES image ESI having substantially the same quality as that in a case in which one radiation tube 15 is used.

In addition, as illustrated in FIGS. 2 and 3, the cathode 30 is a field emission type having an electron emission source that emits electron beams using the field emission phenomenon. The cathode 30 of the field emission type can generate the radiation R at a shorter interval than the cathode with a filament structure which emits thermal electrons. Therefore, it is possible to increase the number of ES images ESI acquired per unit time.

In this embodiment, two radiation tubes 15, that is, the first radiation tube 151 generating the first radiation R1 and the second radiation tube 152 generating the second radiation R2 are used. Therefore, it is possible to reduce the load applied to the radiation tubes 15, as compared to a case in which one radiation tube 15 is used. In addition, since the emission interval between the first radiation R1 and the second radiation R2 in the two-shot imaging operation is reduced to the limit, it is possible to almost eliminate the influence of the body motion of the subject H from the first radiographic image RI1 and the second radiographic image RI2.

The number of radiation tubes 15 may be 2 or more or may be 1. Even in a case in which one radiation tube 15 is used, the emission interval between the first radiation R1 and the second radiation R2 in the two-shot imaging operation is reduced by using the cathode 30 of the field emission type. Therefore, it is possible to eliminate the influence of the body motion of the subject H from the first radiographic image RI1 and the second radiographic image RI2.

Figure 14:
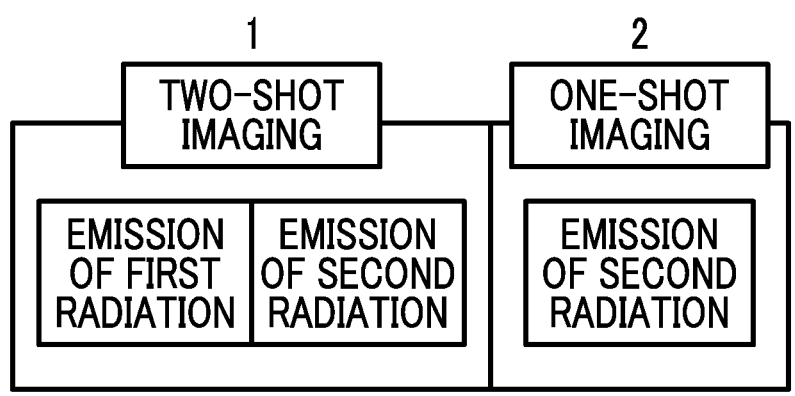
FIG. 14 is a diagram illustrating an imaging mode in which each of a two-shot imaging operation and a one-shot imaging operation is performed once.
Figure 15:
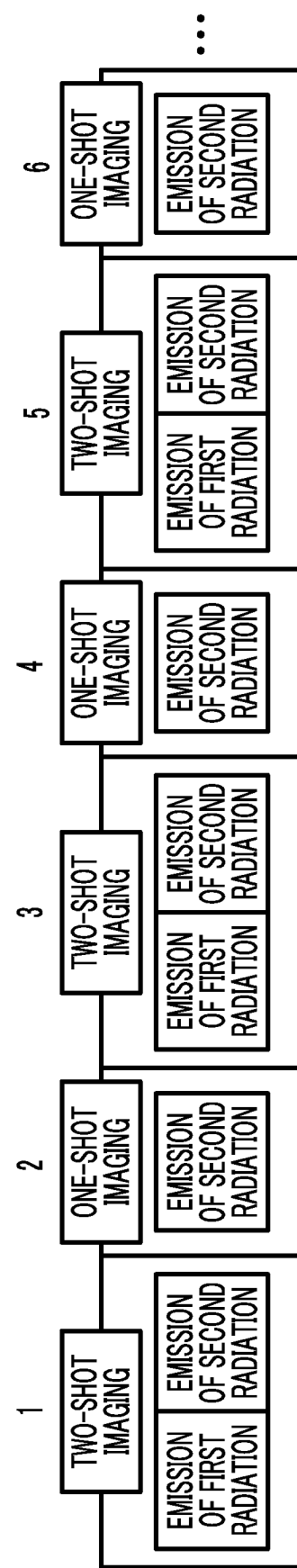
FIG. 15 is a diagram illustrating an imaging mode in which the two-shot imaging operation and the one-shot imaging operation are alternately performed.
Figure 16:
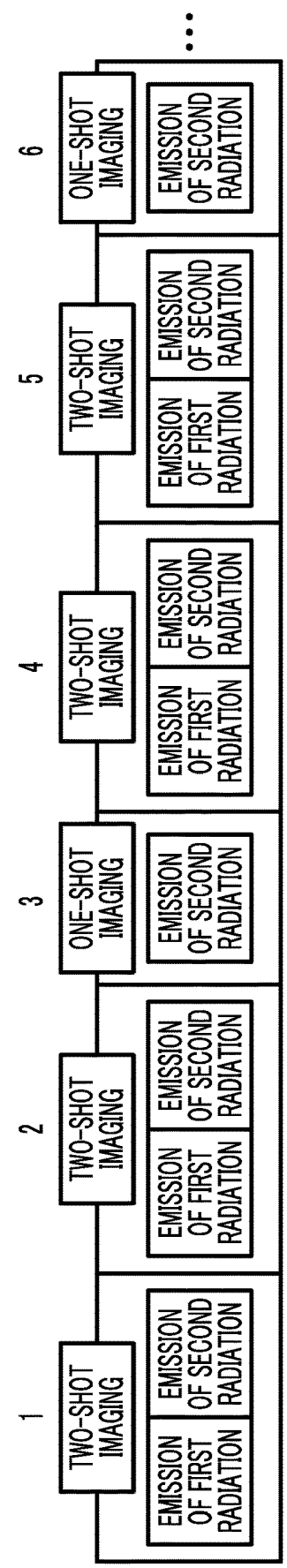
FIG. 16 is a diagram illustrating an imaging mode in which the one-shot imaging operation is performed once during a predetermined number of two-shot imaging operations.

FIGS. 14 to 17 are diagrams illustrating variations in the imaging mode that continuously acquires a plurality of ES images ESI. In FIGS. 14 to 16, the first radiographic image RI1 and the second radiographic image RI2 are not illustrated.

FIG. 14 illustrates an imaging mode in which each of the two-shot imaging operation and the one-shot imaging operation is performed only once. In this case, only two ES images ESI are acquired. As such, the imaging mode is not limited to the moving image capture mode described in the first embodiment which continuously acquires a plurality of ES images ESI required for the display of a moving image according to the predetermined frame interval FI.

FIG. 15 illustrates an imaging mode (moving image capture mode) in which the two-shot imaging operation and the one-shot imaging operation are alternately performed. FIG. 16 illustrates an imaging mode (moving image capture mode) in which the one-shot imaging operation is performed once during a predetermined number of (here, two) two-shot imaging operations. As such, the number of one-shot imaging operations may be equal to the number of two-shot imaging operations or the number of two-shot imaging operations may be larger than the number of one-shot imaging operations. The two-shot imaging operation may be performed only once at the beginning and then the one-shot imaging operation may be continuously performed a plurality of times, which is not illustrated. In short, any aspect may be used as long as it can reduce the amount of radiation R as compared to a case in which the two-shot imaging operation is continuously performed a plurality of times.

Figure 17:
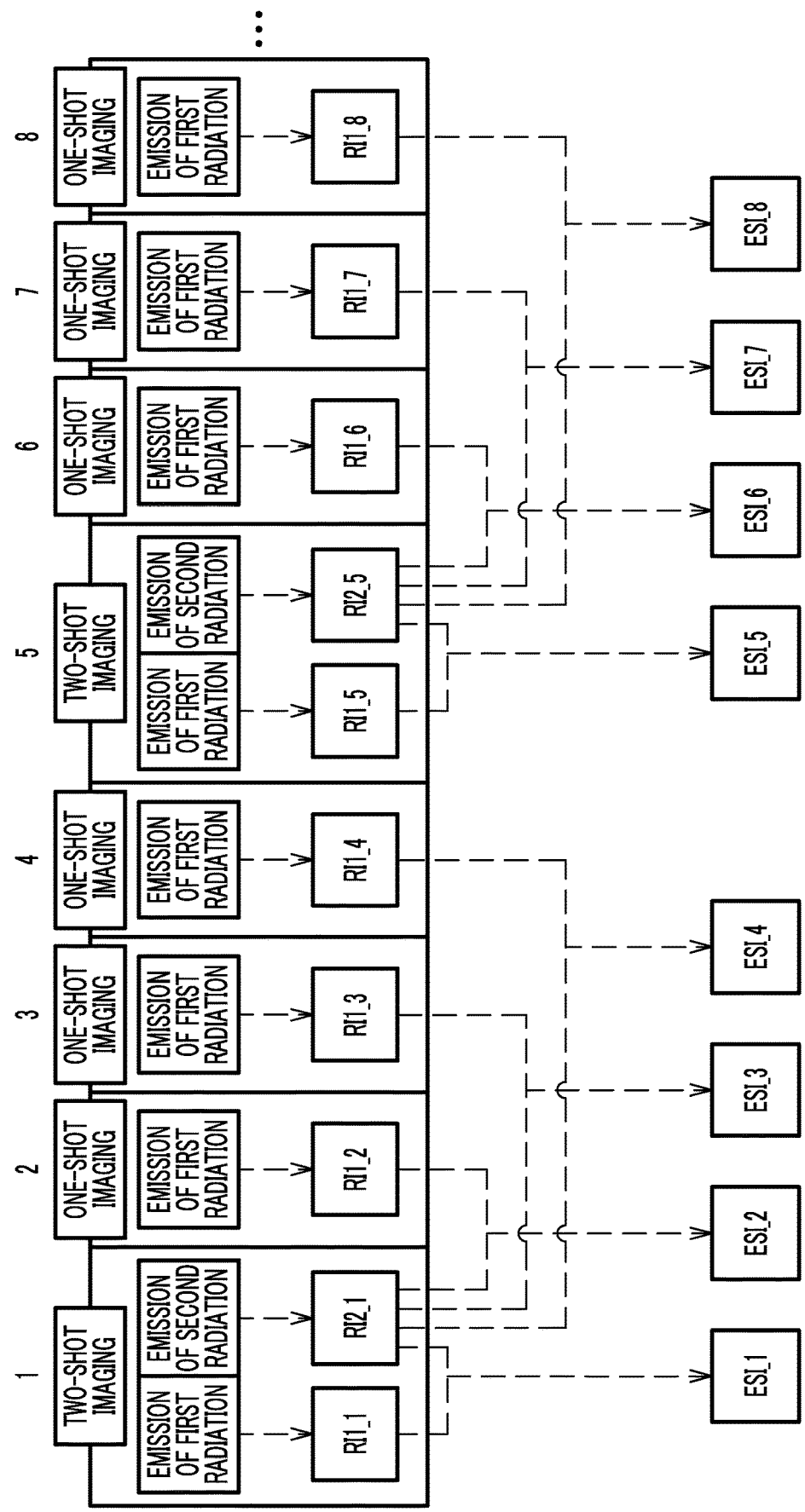
FIG. 17 is a diagram illustrating an aspect in which not the second radiation but only the first radiation is emitted in the one-shot imaging operation.

FIG. 17 illustrates an aspect in which not the second radiation R2 but only the first radiation R1 is emitted in the one-shot imaging operation. In this case, the first radiation R1 is an example of "one of the first radiation and the second radiation" according to the technology of the present disclosure. In addition, the first radiographic image RI1 is an example of "one of the first radiographic image and the second radiographic image" according to the technology of the present disclosure. Conversely, the second radiographic image RI2 is an example of "the other of the first radiographic image and the second radiographic image" according to the technology of the present disclosure.

In the method of generating the ES image ESI, the first radiographic image RI1 and the second radiographic image RI2 in the example illustrated in FIG. 11 are reversed. For example, the ES image ESI_2 of frame 2 is generated on the basis of the second radiographic image RI2_1 of the frame 1 which is the most recent two-shot imaging operation and a first radiographic image RI1_2. Further, for example, an ES image ESI_8 of frame 8 is generated on the basis of a second radiographic image RI2_5 of frame 5 which is the most recent two-shot imaging operation and a first radiographic image RI1_8.

Second Embodiment

In a second embodiment illustrated in FIGS. 18 to 21, the two-shot imaging operation is performed in a case in which it is detected that the body of the subject H has moved at the timing when the one-shot imaging operation is to be performed.

Figure 18:
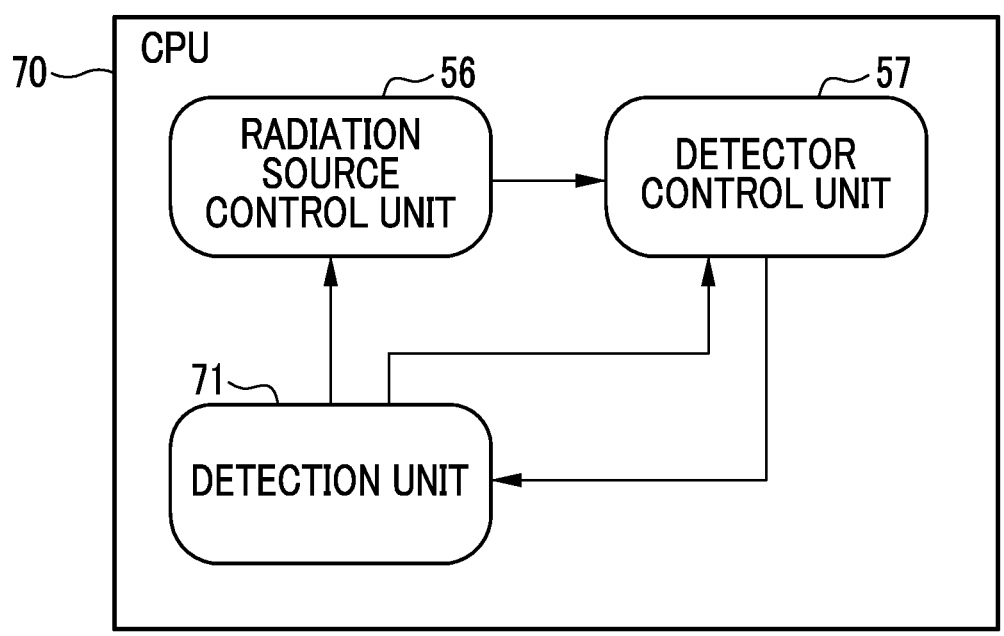
FIG. 18 is a block diagram illustrating a CPU of a control device according to a second embodiment.

In FIG. 18, a CPU 70 of a control device according to this embodiment functions as a detection unit 71 in addition to the processing units 55 to 58 (the irradiation condition acquisition unit 55 and the image transmission unit 58 are not illustrated) according to the first embodiment. The detection unit 71 acquires the radiographic image RI from the detector control unit 57 and detects whether or not the body of the subject H has moved on the basis of the radiographic image RI.

The detection unit 71 extracts feature points of the tissues included in the radiographic image RI using a known image recognition technology. The feature points are, for example, the center point of the first thoracic vertebra and the vertex of the right lung. The detection unit 71 calculates the amount of positional deviation between the feature point of the radiographic image RI of the previous frame and the feature point of the radiographic image RI of the next frame. In addition, the amount of positional deviation is less than a preset threshold value, the detection unit 71 detects that the body of the subject H has not moved. On the other hand, in a case in which the amount of positional deviation is equal to or greater than the threshold value, the detection unit 71 detects that the body of the subject H has moved. The detection unit 71 outputs the detection result to the radiation source control unit 56 and the detector control unit 57. The radiation source control unit 56 performs radiation source control for performing the two-shot imaging operation in a case in which the detection unit 71 detects that the body of the subject H has moved at the timing when the one-shot imaging operation is to be performed.

Figure 20:
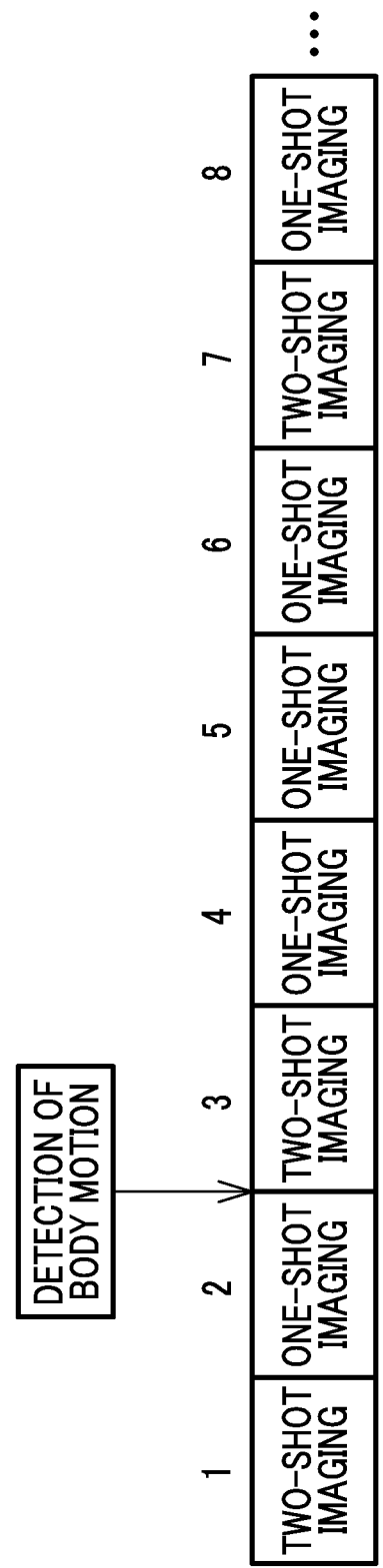
FIG. 20 is a diagram illustrating an imaging mode in which the one-shot imaging operation is performed three times again starting from the two-shot imaging operation performed in a case in which it is detected that the body of the subject has moved.
Figure 21:
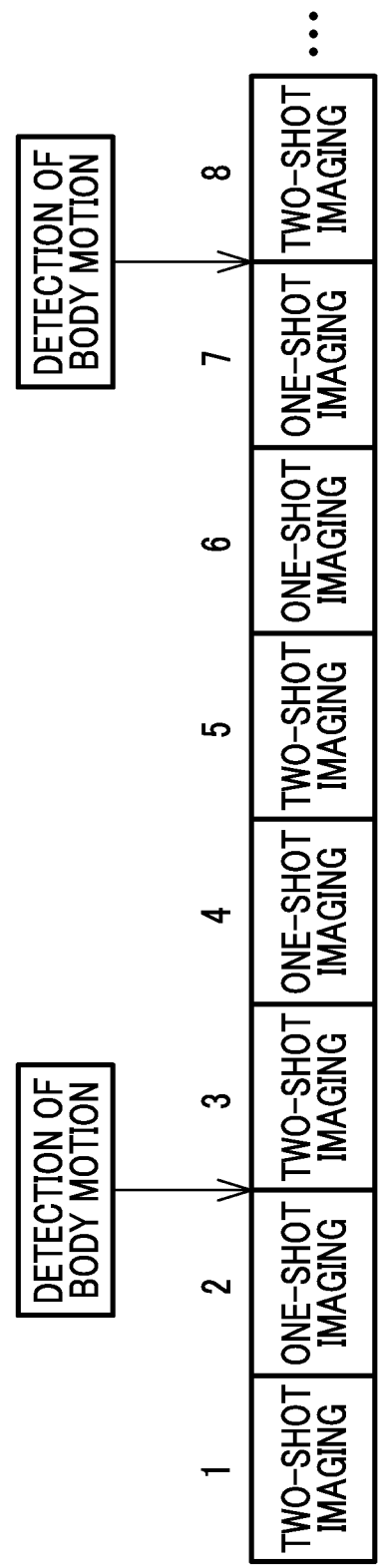
FIG. 21 is a diagram illustrating an imaging mode in which the two-shot imaging operation is performed instead of the one-shot imaging operation, without breaking the rule that the set of one two-shot imaging operation and three one-shot imaging operations is repeatedly performed, in a case in which it is detected that the body of the subject has moved.

For example, the case of an imaging mode in which a set of one two-shot imaging operation and three one-shot imaging operations is repeatedly performed as illustrated in FIG. 19 is considered. In this case, as illustrated in FIGS. 20 and 21, the radiation source control unit 56 performs radiation source control for performing the two-shot imaging operation instead of the one-shot imaging operation in a case in which the detection unit 71 detects that the body of the subject H has moved at the timing when the one-shot imaging operation is to be originally performed. FIG. 20 illustrates an example of an imaging mode in which the one-shot imaging operation is performed three times again starting from the two-shot imaging operation performed in a case in which it is detected that the body of the subject H has moved. In contrast, FIG. 21 illustrates an example of an imaging mode in which the two-shot imaging operation is performed instead of the one-shot imaging operation, without breaking the rule that the two-shot imaging operation is performed once and the one-shot imaging operation is performed three times, in a case in which it is detected that the body of the subject H has moved.

As such, in the imaging mode according to the second embodiment, in a case in which the detection unit 71 detects that the body of the subject H has moved at the timing when the one-shot imaging operation is to be performed, the two-shot imaging operation is performed. That is, of the first radiographic image RI1 and the second radiographic image RI2 output in the most recent two-shot imaging operation, the other radiographic image which is reused to generate the ES image ESI corresponding to the one-shot imaging operation is updated in a case in which the body motion of the subject H is detected. Therefore, it is possible to effectively remove the influence of the body motion from the ES image ESI and to contribute to improving the quality of the ES image ESI.

The cold cathode is not limited to the field emission type. The cold cathode may be any type other than the thermal electron emission type. Further, the cathode 30 is not limited to the cold cathode and may be a hot cathode.

For example, the following imaging modes may be used: an imaging mode for performing the ES imaging according to the related art which is completed by one two-shot imaging operation; and an imaging mode for simply acquiring a still radiographic image instead of the ES imaging.

In the two-shot imaging operation, first, the second radiation R2 may be emitted and the second radiographic image RI2 may be output. Then, the first radiation R1 may be emitted and the first radiographic image RI1 may be output.

The control device 13 and the console 14 may be integrated into one device. Further, the control device 13 may be divided into a radiation source control device that controls the operation of the radiation source 10 and a detector control device that controls the operation of the radiation detector 11. The radiation source control unit 56 may be provided in the radiation source control device and the detector control unit 57 may be provided in the detector control device.

In the above-described embodiments, for example, the following various processors can be used as the hardware structure of processing units performing various processes, such as the irradiation condition acquisition unit 55, the radiation source control unit 56, the detector control unit 57, the image transmission unit 58, and the detection unit 71. The various processors include a central processing unit (CPU) which is a general-purpose processor executing software to function as various processing units, a programmable logic device (PLD), such as a field programmable gate array (FPGA), which is a processor whose circuit configuration can be changed after manufacture, and a dedicated electric circuit, such as an application specific integrated circuit (ASIC), which is a processor having a dedicated circuit configuration designed to perform a specific process.

One processing unit may be configured by one of the various processors or a combination of two or more processors of the same type or different types (for example, a combination of a plurality of FPGAs or a combination of a CPU and an FPGA). In addition, a plurality of processing units may be configured by one processor.

A first example of the configuration in which a plurality of processing units are configured by one processor is an aspect in which one processor is configured by a combination of one or more CPUs and software and functions as a plurality of processing units. A representative example of this aspect is a client computer or a server computer. A second example of the configuration is an aspect in which a processor that implements the functions of the entire system including a plurality of processing units using one integrated circuit (IC) chip is used. A representative example of this aspect is a system-on-chip (SoC). As such, various processing units are configured by using one or more of the various processors as a hardware structure.

In addition, specifically, an electric circuit (circuitry) obtained by combining circuit elements, such as semiconductor elements, can be used as the hardware structure of the various processors.

It is possible to understand the invention described in the following Supplementary Note 1 from the above description.

Supplementary Note 1

There is provided a radiography apparatus comprising: a radiation source that emits radiation; a radiation detector that detects the radiation transmitted through a subject and outputs a radiographic image of the subject; a radiation source control processor that performs control to direct the radiation source to emit first radiation with a first energy distribution and second radiation with a second energy distribution different from the first energy distribution in order to acquire an energy subtraction image in which a structure in the subject has been highlighted and performs radiation source control for performing a one-shot imaging operation, in which only one of the first radiation and the second radiation is emitted, at least once for one two-shot imaging operation, in which the first radiation and the second radiation are continuously emitted, in a case in which an imaging mode continuously acquiring a plurality of the energy subtraction images is performed; and a detector control processor that performs detector control to direct the radiation detector to output a first radiographic image based on the first radiation and a second radiographic image based on the second radiation in a case in which the imaging mode is performed.

In addition, the technology according to the present disclosure includes the invention described in the following Supplementary Notes 2 to 5.

Supplementary Note 2

There is provided a control device that controls a radiography apparatus comprising a radiation source that emits radiation and a radiation detector that detects the radiation transmitted through a subject and outputs a radiographic image of the subject. The control device comprises: a radiation source control unit that performs control to direct the radiation source to emit first radiation with a first energy distribution and second radiation with a second energy distribution different from the first energy distribution in order to acquire an energy subtraction image in which a structure in the subject has been highlighted and performs radiation source control for performing a one-shot imaging operation, in which only one of the first radiation and the second radiation is emitted, at least once for one two-shot imaging operation, in which the first radiation and the second radiation are continuously emitted, in a case in which an imaging mode continuously acquiring a plurality of the energy subtraction images is performed; and a detector control unit that performs detector control to direct the radiation detector to output a first radiographic image based on the first radiation and a second radiographic image based on the second radiation in a case in which the imaging mode is performed.

Supplementary Note 3

There is provided a method for operating a control device that controls a radiography apparatus comprising a radiation source that emits radiation and a radiation detector that detects the radiation transmitted through a subject and outputs a radiographic image of the subject. The method comprises: a radiation source control step of performing control to direct the radiation source to emit first radiation with a first energy distribution and second radiation with a second energy distribution different from the first energy distribution in order to acquire an energy subtraction image in which a structure in the subject has been highlighted and performing radiation source control for performing a one-shot imaging operation, in which only one of the first radiation and the second radiation is emitted, at least once for one two-shot imaging operation, in which the first radiation and the second radiation are continuously emitted, in a case in which an imaging mode continuously acquiring a plurality of the energy subtraction images is performed; and a detector control step of performing detector control to direct the radiation detector to output a first radiographic image based on the first radiation and a second radiographic image based on the second radiation in a case in which the imaging mode is performed.

Supplementary Note 4

There is provided a program for operating a control device that controls a radiography apparatus comprising a radiation source that emits radiation and a radiation detector that detects the radiation transmitted through a subject and outputs a radiographic image of the subject. The program causes a computer to function as: a radiation source control unit that performs control to direct the radiation source to emit first radiation with a first energy distribution and second radiation with a second energy distribution different from the first energy distribution in order to acquire an energy subtraction image in which a structure in the subject has been highlighted and performs radiation source control for performing a one-shot imaging operation, in which only one of the first radiation and the second radiation is emitted, at least once for one two-shot imaging operation, in which the first radiation and the second radiation are continuously emitted, in a case in which an imaging mode continuously acquiring a plurality of the energy subtraction images is performed; and a detector control unit that performs detector control to direct the radiation detector to output a first radiographic image based on the first radiation and a second radiographic image based on the second radiation in a case in which the imaging mode is performed.

Supplementary Note 5

There is provided a control device that controls a radiography apparatus comprising a radiation source that emits radiation and a radiation detector that detects the radiation transmitted through a subject and outputs a radiographic image of the subject. The control device comprises: a radiation source control processor that performs control to direct the radiation source to emit first radiation with a first energy distribution and second radiation with a second energy distribution different from the first energy distribution in order to acquire an energy subtraction image in which a structure in the subject has been highlighted and performs radiation source control for performing a one-shot imaging operation, in which only one of the first radiation and the second radiation is emitted, at least once for one two-shot imaging operation, in which the first radiation and the second radiation are continuously emitted, in a case in which an imaging mode continuously acquiring a plurality of the energy subtraction images is performed; and a detector control processor that performs detector control to direct the radiation detector to output a first radiographic image based on the first radiation and a second radiographic image based on the second radiation in a case in which the imaging mode is performed.

In the technology according to the present disclosure, the above-mentioned various embodiments and various modification examples may be combined with each other. In addition, the present disclosure is not limited to each of the above-described embodiments and various configurations can be used without departing from the scope and spirit of the present disclosure. Further, the technology according to the present disclosure may be applied to a storage medium that non-temporarily stores the program in addition to the program.

The contents described and illustrated above are the detailed description of portions related to the technology according to the present disclosure and are merely examples of the technology according to the present disclosure. For example, the description of the configurations, the functions, the operations, and the effects is the description of an example of the configurations, functions, operations, and effects of a portion according to the technology of the present disclosure. Therefore, for the contents described and illustrated above, unnecessary portions may be deleted or new elements may be added or replaced without departing from the scope and spirit of the technology according to the present disclosure. In the contents described and illustrated above, the description of common technical knowledge that does not require any explanation in order to enable the implementation of the technology according to the present disclosure is omitted in order to avoid complications and to facilitate the understanding of the portions related to the technology according to the present disclosure.

All of the documents, the patent applications, and the technical standards described in the specification are incorporated by reference to the same extent as the incorporation of each of the documents, the patent applications and the technical standards by reference is specifically and individually stated.

What is claimed is:

1. A radiography apparatus comprising:
a radiation source that emits radiation;
a radiation detector that detects the radiation transmitted through a subject and outputs a radiographic image of the subject;
a radiation source control unit that performs control to direct the radiation source to emit a first radiation with a first energy distribution and a second radiation with a second energy distribution different from the first energy distribution in order to acquire an energy subtraction image in which a structure in the subject has been highlighted, and performs radiation source control for performing a one-shot imaging operation, in which only one of the first radiation or the second radiation is emitted, at least once for each two-shot imaging operation, in which the first radiation and the second radiation are continuously emitted, in a case in which an imaging mode continuously acquiring a plurality of energy subtraction images is performed; and
a detector control unit that performs detector control to direct the radiation detector to output a first radiographic image based on the first radiation and a second radiographic image based on the second radiation in a case in which the imaging mode is performed,
wherein, in the imaging mode, a number of one-shot imaging operations is larger than a number of two-shot imaging operations.

2. The radiography apparatus according to claim 1, wherein the imaging mode is a moving image capture mode that continuously acquires a plurality of energy subtraction images required for displaying a moving image according to a predetermined frame interval.

3. The radiography apparatus according to claim 1, wherein an energy subtraction image corresponding to the two-shot imaging operation is generated on the basis of a first radiographic image and a second radiographic image output from the radiation detector in the two-shot imaging operation, and
an energy subtraction image corresponding to the one-shot imaging operation is generated on the basis of one of a first radiographic image or a second radiographic image output from the radiation detector in the one-shot imaging operation and on the basis of another of the first radiographic image or the second radiographic image output from the radiation detector in the two-shot imaging operation, immediately before the one-shot imaging operation.

4. The radiography apparatus according to claim 1, wherein, in the imaging mode, the two-shot imaging operation is performed once during a predetermined number of one-shot imaging operations.

5. The radiography apparatus according to claim 1, further comprising:
a detection unit that detects whether or not a body of the subject has moved,
wherein, in the imaging mode, the two-shot imaging operation is performed in a case in which the detection unit detects that the body of the subject has moved at a timing when the one-shot imaging operation is to be performed.

6. The radiography apparatus according to claim 1, wherein the radiation source includes a radiation tube having a cold cathode.

7. The radiography apparatus according to claim 1, wherein an intensity of the second radiation in the second energy distribution is lower than an intensity of the first radiation in the first energy distribution, and
the radiation source control unit directs the radiation source to emit only the second radiation in the one-shot imaging operation.

8. The radiography apparatus according to claim 6, wherein the cold cathode is a field emission type having an electron emission source that emits an electron beam using a field emission phenomenon.

9. The radiography apparatus according to claim 6, wherein at least two radiation tubes of a first radiation tube that generates the first radiation and a second radiation tube that generates the second radiation are provided as the radiation tube.

10. A method for operating a radiography apparatus comprising a radiation source that emits radiation and a radiation detector that detects the radiation transmitted through a subject and outputs a radiographic image of the subject, the method comprising:
a radiation source control step of performing control to direct the radiation source to emit a first radiation with a first energy distribution and a second radiation with a second energy distribution different from the first energy distribution in order to acquire an energy subtraction image in which a structure in the subject has been highlighted and performing radiation source control for performing a one-shot imaging operation, in which only one of the first radiation or the second radiation is emitted, at least once for each two-shot imaging operation, in which the first radiation and the second radiation are continuously emitted, in a case in which an imaging mode continuously acquiring a plurality of energy subtraction images is performed; and
a detector control step of performing detector control to direct the radiation detector to output a first radiographic image based on the first radiation and a second radiographic image based on the second radiation in a case in which the imaging mode is performed, wherein, in the imaging mode, a number of one-shot imaging operations is larger than a number of two-shot imaging operations.

11. A non-transitory computer-readable storage medium storing a program for operating a radiography apparatus comprising a radiation source that emits radiation and a radiation detector that detects the radiation transmitted through a subject and outputs a radiographic image of the subject, the program causing a computer to function as:
a radiation source control unit that performs control to direct the radiation source to emit a first radiation with a first energy distribution and a second radiation with a second energy distribution different from the first energy distribution in order to acquire an energy subtraction image in which a structure in the subject has been highlighted and performs radiation source control for performing a one-shot imaging operation, in which only one of the first radiation or the second radiation is emitted, and at least once for each two-shot imaging operation, in which the first radiation and the second radiation are continuously emitted, in a case in which an imaging mode continuously acquiring a plurality of energy subtraction images is performed; and
a detector control unit that performs detector control to direct the radiation detector to output a first radiographic image based on the first radiation and a second radiographic image based on the second radiation in a case in which the imaging mode is performed,
wherein, in the imaging mode, a number of one-shot imaging operations is larger than a number of two-shot imaging operations.

* * * * *